United States Patent [19]

Tsuji et al.

[11] 4,220,766
[45] Sep. 2, 1980

[54] OXAZOLINES

[75] Inventors: Teruji Tsuji, Takatsuki; Mitsuru Yoshioka; Shoichiro Uyeo, both of Toyonaka; Yoshio Hamashima, Kyoto; Ikuo Kikkawa, Takarazuka; Wataru Nagata, Nishinomiya, all of Japan

[73] Assignee: Shionogi & Co., Ltd., Osaka, Japan

[21] Appl. No.: 868,422

[22] Filed: Jan. 10, 1978

[30] Foreign Application Priority Data

Jan. 10, 1977 [JP]  Japan .................................. 52-1760
Mar. 30, 1977 [JP]  Japan ................................. 52-36613

[51] Int. Cl.$^2$ .................. C07D 285/16; C07D 491/04
[52] U.S. Cl. ..................................... 544/182; 544/333; 544/405; 546/271; 546/144; 546/170; 546/167; 546/147; 548/125; 548/136; 548/182; 548/218
[58] Field of Search ......................... 544/182, 333, 405; 546/271, 144, 170, 167, 147; 260/307 F, 306.8 R, 306.8 A, 306.8 D

[56]  References Cited
U.S. PATENT DOCUMENTS 3,864,339  2/1975  Thomas ................................ 260/243
3,950,352  4/1976  Wolfe ..................................... 260/307

Primary Examiner—John M. Ford
Attorney, Agent, or Firm—Wenderoth, Lind & Ponack

[57]  ABSTRACT

Useful intermediates for preparing a 1-dethia-1-oxacephalosporin and represented by the following formula:

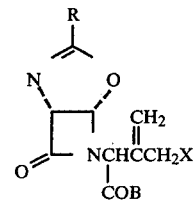

(wherein
R is a monovalent group resulting from the elimination of the carbonyl function of an acyl group derived from a carboxylic or carbonic acid;
COB is carboxy or protected carboxy; and
X is hydrogen or a nucleophilic group)
are prepared from the corresponding penicillin 1-oxides of the following formula:

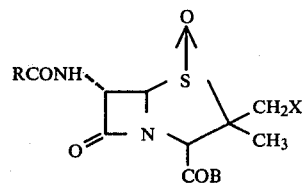

(wherein R, COB, and X are as defined above)
by heating, if required in the presence of the desulfurizing reagent, or by exchanging the X group with another one under the condition of an appropriate nucleophilic substitution.

4 Claims, No Drawings

OXAZOLINES

This invention relates to oxazolinoazetidine compounds (I) useful as intermediates for preparing antibacterial 1-oxadethiacephalosporins, and a process for preparing them.

I. COMPOUNDS

The Compounds (I) of this invention are shown by the following formula:

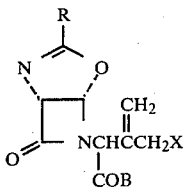

(wherein
R is a monovalent residue resulting from the dimination of the carbonyl function of an acyl group derived from a carboxylic or carbonic acid;
COB is carboxy or protected carboxy; and
X is hydrogen or a nucleophilic group).

The said group R is a monovalent group of acylminus-carbonyl derived from carboxylic or carbonic acyls shown by partial formula RCO—, and preferably containing from 1 to 15 carbon atoms. Typical examples of R include hydrogen, 1–6 C alkyl (e.g. methyl, ethyl, propyl, isopropyl, butyl, t-butyl, cyclopentylmethyl), 7–15 C aralkyl (e.g. benzyl, phenethyl, diphenylmethyl), 7–9 C aryloxyalkyl (e.g. phenoxymethyl, phenoxyethyl, phenoxypropyl), 6–10 C aryl (e.g. phenyl, naphthyl), 1–6 C alkoxy (e.g. methoxy, ethoxy, propoxy, cyclopropylmethoxy, cyclohexyloxy), 7–15 C aralkoxy (e.g. benzyloxy, phenethyloxy), 6–10 C aryloxy (e.g. phenoxy, naphthyloxy), carbamoyl, 2–7 C carbalkoxy, and the like monovalent groups. These can further be substituted with another group e.g. hydroxy, 1–6 C acyloxy, 1–3 C alkoxy, oxo, amino, 1–3 C alkylamino, 1–6 C acylamino, nitro, 1–3 C alkyl, 6–10 C aryl, carboxy, protected carboxy, cyano; halo, 1–3 C alkyl or like substituents, or can optionally be unsaturated. The aryl part of said groups can also be five or six membered carbocyclic or heterocyclic aromatic group including phenyl, naphthyl, furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyrazinyl, pyridazinyl, triazinyl, quinolyl, isoquinolinyl, and benzothiazolyl.

Specific examples of R group include hydrogen, methyl, ethyl, propyl, isopropyl, butyl, methoxymethyl, carbethoxy, trichloroethoxycarbonyl, acetoxyethyl, chloroethyl, allyl, benzyl, nitrobenzyl, chlorobenzyl, aminobenzyl, acetamidobenzyl, bromobenzyl, methoxybenzyl, ethoxybenzyl, methylenedioxybenzyl, trimethoxybenzyl, dichlorobenzyl, hydroxybenzyl, phenethyl, chlorophenethyl, methylphenethyl, nitrophenethyl, methoxyphenethyl, diphenylmethyl, α-chlorobenzyl, α-bromobenzyl, benzyloxybenzyl, anisyloxybenzyl, α-protected carboxybenzyl, α-protected carboxy-p-anisyloxybenzyl, α-protected carboxy-p-diphenylmethoxybenzyl, α-protected carboxyacetyloxybenzyl, furylmethyl, thienylmethyl, oxazolylmethyl, isoxazolylmethyl, thiazolylmethyl, thiadiazolylmethyl, pyrazolylmethyl, tetrazolylmethyl, α-carbalkoxy-α-thienylmethyl, carbomethoxy, carbethoxy, benzyloxycarbonyl, carbamoyl, phenoxymethyl, phenoxyethyl, phenoxypropyl, phenoxybutyl, isoxazolyloxymethyl, phenyl, tolyl, xylyl, hydroxyphenyl, acetoxyphenyl, methoxyphenyl, t-butyloxyphenyl, nitrophenyl, cyanophenyl, carbethoxyphenyl, aminophenyl, acetamidophenyl, methylaminophenyl, chlorophenyl, bromophenyl, thienyl, furyl, pyrrolyl, oxazolyl, oxadiazolyl, oxatriazolyl, thiazolyl, thiadiazolyl, pyrazolyl, triazolyl, tetrazolyl, pyridyl, t-butoxy, cyclopropylmethoxy, cyclopropylethoxy, cyclopentyloxy, methanesulfonylethoxy, trichloroethoxy, phenacyloxy, benzyloxy, xylyloxy, diphenylmethoxy, phenoxy, tolyloxy, naphthyloxy, pentachlorophenoxy, nitrobenzyloxy, pyridyloxy, and benzothiazolyloxy.

The group RCO— can be removed or introduced when desired, and the structure thereof can be varied widely or easily exchangeable regardless of process phases of the starting or produced material in whole course of synthesis. The structure of choice can be selected in consideration of stability during the reaction and work-up.

The protected carboxy COB, preferably containing up to 20 carbon atoms, is conventional one in the field of β-lactam antibiotics and must tolerate under the reaction condition of this invention. Preferably, said carboxy for COB is protected in the forms of, for example, ester [e.g. 1-5 C alkyl (e.g. methyl, ethyl, t-butyl, cyclopropylmethyl), 7–20 C aralkyl (e.g. benzyl, phenethyl, diphenylmethyl, trityl), 6–10 C aryl (e.g. phenyl, indanyl, naphthyl), or 3–10 C organometallic (e.g. trimethylsilyl, ethoxydimethylsilyl, trimethylstannyl) esters], 1–8 C amide (e.g. dimethylamide, dibutylamide, diisopropylhydrazide), alkali metal salt (e.g. lithium, sodium, or potassium salt), alkaline earth metal salt (e.g. magnesium, calcium, barium salt), aluminum salt, acid anhydride, or acid halide. The protecting part B may have further substituent such as halo, hydroxy, 1–5 C acyloxy, oxo, 1–5 C acylamino, nitro, 1–3 C alkyl, carboxy, 2–6 C carbalkoxy, 1–5 C acyl, cyano, and its aryl part may be a heteroaromatic ring group. Generally, the protecting group is removed after the reaction, and its structure can widely be varied without changing the gist of this invention, when suitable for the protection.

Specific examples of COB group include optionally substituted alkyl esters e.g. methyl, ethyl, isopropyl, propyl, butyl, pentyl, cyclopropylmethyl, cyclopropylethyl, cyclopropylbutyl, monohydroxy-t-butyl, trichloroethyl, chloromethyl, cyanomethyl, methanesulfonylethyl, acetylmethyl, diacetylmethyl, acetoxymethyl, propionyloxymethyl, benzoyloxymethyl, methoxymethyl, methoxyethoxymethyl, carbethoxymethyl, phenoxymethyl, methylthiomethyl, phenylthiomethyl, tetrahydropyranyl, phthalimidomethyl, α,α-dimethylpropargyl, ethoxycarbonyloxyethyl, methoxycarbonyloxypropyl, and allylesters; aralkyl esters e.g. benzyl, phenethyl, tolylmethyl, dimethylbenzyl, nitrobenzyl, halobenzyl, methoxybenzyl, phthalidyl, anthrylmethyl, p-hydroxy-3,5-di-t-butylbenzyl, diphenylmethyl, methoxydiphenylmethyl, trityl, phenacyl, chlorophenacyl, bromophenacyl, nitrophenacyl, and methylphenacyl esters; aromatic esters e.g. phenyl, naphthyl, tolyl, dimethylphenyl, nitrophenyl, methanesulfonylphenyl, chlorophenyl, pentachlorophenyl, indanyl, and pyridyl esters; and organometallic esters e.g. trimethylsilyl, dimethylmethoxysilyl, methylenedioxymethylsilyl, trimethylstannyl esters; alkali metal or alkaline earth metal salts e.g. sodium, potassium, magnesium, calcium, aluminum, acyloxycalcium, and barium salts, organic base salts e.g. triethylammonium and dicyclohexylammonium salt; mixed anhydride with acetic acid or 1–5 C alkyl half carboxylate; and in some cases, chloride and bromide.

The nucleophilic group X includes every possible group introduced in place of the acetoxy attached to the methylene at position 3 of cephalosporins, and containing preferably up to 15 carbon atoms.

Typical examples of X include halo (e.g. chloro, bromo, iodo), hydroxy, up to 5 C acyloxy (e.g. nitrooxy, sulfurous acyloxy, formyloxy, acetoxy, propionyloxy, trifluoroacetoxy, β-hydroxypropionyloxy, α-haloacetyloxy, β-hydroxypropionyloxy, benzoyloxy, nicotinoyloxy, carbamoyloxy, methoxycarbonyloxy, aminopropionyloxy, sulfenyloxy, sulfinyloxy), 1–6 C alkoxy (e.g. methoxy, ethoxy, butoxy, cyclohexyloxy, cyclopropylmethoxy, tetrahydropyranyloxy), thiocarbamoylthio, 1–5 C alkylthio, 6–10 C arylthio (e.g. phenylthio, naphthylthio, thienylthio, 1-methyltetrazolylthio, 1-methanesulfonylethyl-5-tetrazolylthio, 1-carboxyethyl-5-tetrazolylthio, 1-protected carboxyethyl-5-tetrazolylthio, 1-protected sulfonylethyl-5-tetrazolylthio, 1-methylaminoethyl-5-tetrazolylthio, 1-dimethylaminoethyl-5-tetrazolylthio, 1-dimethylaminoethyl-5-tetrazolylthio, 1-morpholinoethyl-5-tetrazolylthio, 1,3,4-thiadiazol-5-ylthio, 2-methyl-1,3,4-thiadiazol-5-ylthio, 2-carboxymethyl-1,3,4-thiadiazol-5-ylthio, 2-protected carboxymethyl-1,3,4-thiadiazol-5-ylthio, 2-protected hydroxymethyl-1,3,4-thiadiazol-5-ylthio, 2-aminomethyl-1,3,4-thiadiazol-5-ylthio, 2-methylaminomethyl-1,3,4-thiadiazol-5-ylthio, 1,2,3-triazol-4-ylthio, 1-methyl-5-hydroxy-6-oxo-1,6-dihydro-1,3,4-triazin-2-ylthio), 1–6 C alkylsulfinyl (e.g. ethylsulfinyl, phenylsulfinyl, 1-methyl-5-tetrazolylsulfinyl), and the like nucleophilic groups.

Preferable X is a leaving group for a successive substitution e.g. halo, haloalkanoyloxy, or sulfonyloxy cited above. Alternatively, it is an aimed group bound for the final antibacterial, being a function linked to the methylene at position 3 of 1-oxadethiacepham nucleus e.g. hydrogen, lower alkanoyloxy, carbamoyloxy, and heteroaromatic thio cited above.

When R, COB, or X each seems to be suffered from unfavorable damages during the reaction, such a weak point can be protected in advance and deprotected at an optional and desirable stage after the reaction. Such a desirable treatment is also included in the scope of this invention. For example, carboxy and hydroxy present in these group can be protected if desired by conventional methods well known in β-lactam chemistry with e.g. carboxy-protecting group cited for COB and acyl or ether protecting for hydroxy.

Some of representative examples of Compounds (I) are given in Examples described below, but other variations of R and X are possible because they are also exchangeable with other group within the definition during the synthesis. Further, carboxy-protecting group can be conventional ones in the field of penicillin and cephalosporin chemistry.

As stated above, Compounds I are represented by the following formula:

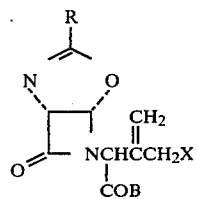

(wherein
R is a monovalent group resulting from the elimination of the carbonyl function of an acyl moiety derived from a carboxylic or carbonic acid;
COB is carboxy or protected carboxy conventional in penicillin and cephalosporin chemistry; and
X is hydrogen or a nucleophilic group).

Among them, more preferable ones have following figures: R is 1–6 C alkyl, 7–15 C aralkyl, 7–9 C aryloxyalkyl, 6–10 C aryl, 1–6 C alkoxy, 7–15 C aralkoxy, 6–10 C aryloxy, carbamoyl or 2–7 C carbalkoxy, each being optionally substituted by hydroxy, 1–6 C acyloxy (e.g. formyloxy, acetoxy, propionyloxy, pentanoyloxy), 1–3 C alkoxy (e.g. methoxy, ethoxy, propoxy), 7–9 C aralkoxy (e.g. benzyloxy, tolylmethoxy, xylylmethoxy, anisyloxy, nitrobenzyloxy, halobenzyloxy), 6–8 C aryloxy (e.g. phenoxy, xylyloxy), oxo, amino, 1–3 C alkylamino (e.g. methylamino, dimethylamino), 1–5 C acylamino (e.g. acetamido, propionamido, valeramido), nitro, 1–3 C alkyl (e.g. methyl, ethyl, propyl), 6–10 C aryl (e.g. phenyl, xylyl), carboxy, protected carboxy, cyano, or halo; X is halo (e.g. chloro, bromo, iodo), hydroxy, up to 5 C acyloxy (e.g. nitroxy, sulfurous oxy, sulfoxy, formyloxy, acetoxy, haloacetoxy, propionyloxy, butyryloxy, pentanoyloxy), 1–6 C alkoxy (e.g. methoxy, propoxy, hexyloxy), thiocarbamoylthio, 1–5 C alkylthio (e.g. methylthio, pentylthio), 6–9 C arylthio (e.g. phenylthio, tolylthio, nitrophenylthio), or 1–6 C sulfinyl (e.g. methylsulfinyl, phenylsulfinyl), provided that said aryl parts in R and X can optionally be heteroaryl; and COB is carboxy or protected carboxy conventional in the chemistry of penicillins and cephalosporins.

More preferable Compounds (I) include those having R being benzyl, phenoxymethyl, or phenyl optionally substituted by methyl, ethyl, propyl, isopropyl, chloro, bromo, cyano, methoxy, ethoxy, propoxy, or nitro; X being hydroxy, chloro, bromo, iodo, nitroxy, sulfoxy, formyloxy, acetoxy, trifluoroacetoxy, trichloroacetoxy, propionyloxy, butyryloxy, phenylthio, methylthio, ethylthio, methyltetrazolylthio, 1-dimethylaminoethyltetrazolylthio, 1-carboxyethyltetrazolylthio, thiadiazolylthio, methylthiadiazolylthio, triazolylthio, 1-methyl-5-hydroxy-6-oxo-1,6-dihydro-1,3,4-triazin-2-ylthio, phenylsulfinyl, or methylsulfinyl, especially X being hydroxy, chloro, bromo, iodo, or nitroxy; and COB being carboxy or protected carboxy forming 1–5 C alkyl ester, 7–20 C aralkyl ester, 6–10 C aryl ester, 3–10 C organometallic ester, 1–8 C amide, alkali metal salt, or alkaline earth metal salt, each optionally substituted by halo, hydroxy, 1–5 C acyloxy (e.g. formyloxy, acetoxy, propionyloxy, butyryloxy, isobutyryloxy, pentanoyloxy), oxo, 1–5 C acylamino (e.g. acetamido, propionamido, valeylamido), nitro, 1–3 C alkyl (e.g. methyl, ethyl, propyl, isopropyl), carboxy, 2–6 C carbalkoxy (e.g. carbomethoxy, carbethoxy, propoxycarbonyl, butoxycarbonyl), 1–5 C acyl (e.g. acetyl, propionyl, butyryl, pentanoyl), or cyano, especially COB being protected carboxy forming methyl ester, tirchloroethyl ester, isopropyl ester, t-butyl ester, benzyl ester, nitrobenzyl ester, methoxybenzyl ester, diphenylmethyl ester, or trityl ester.

Typical examples of Compounds (I) include those where (1) R is phenyl, X is hydrogen, and COB is carboxy;
(2) R is phenyl, X is chloro, and COB is carboxy;
(3) R is phenyl, X is bromo, and COB is carboxy;
(4) R is phenyl, X is iodo, and COB is carboxy;
(5) R is phenyl, X is nitroxy, and COB is carboxy;
(6) R is phenyl, X is formyloxy, and COB is carboxy;
(7) R is phenyl, X is acetoxy, and COB is carboxy;
(8) R is phenyl, X is methylthio, and COB is carboxy;
(9) R is phenyl, X is ethylthio, and COB is carboxy;
(10) R is phenyl, X is phenylthio, and COB is carboxy;
(11) R is phenyl, X is methyltetrazolylthio, and COB is carboxy;
(12) R is phenyl, X is 1-carboxymethyltetrazol-5-ylthio, and COB is carboxy;
(13) R is phenyl, X is thiadiazol-5-ylthio, and COB is carboxy;
(14) R is phenyl, X is methylthiadiazolylthio, and COB is carboxy;
(15) R is phenyl, X is triazol-4-ylthio, and COB is carboxy;
(16) R is phenyl, X is 1-methyl-5-hydroxy-6-oxo-1,6-dihydro-1,3,4-triazin-2-ylthio, and COB is carboxy;
(17) R is phenyl, X is phenylsulfinyl, and COB is carboxy;
(18) R is tolyl, X is hydrogen, and COB is carboxy;
(19) R is tolyl, X is chloro, and COB is carboxy;
(20) R is tolyl, X is bromo, and COB is carboxy;
(21) R is tolyl, X is iodo, and COB is carboxy;
(22) R is tolyl, X is hydroxy, and COB is carboxy;
(23) R is tolyl, X is nitroxy, and COB is carboxy;
(24) R is tolyl, X is formyloxy, and COB is carboxy;
(25) R is tolyl, X is acetoxy, and COB is carboxy;
(26) R is tolyl, X is methylthio, and COB is carboxy;
(27) R is tolyl, X is ethylthio, and COB is carboxy;
(28) R is tolyl, X is phenylthio, and COB is carboxy;
(29) R is tolyl, X is 1-methyltetrazolylthio, and COB is carboxy;
(30) R is tolyl, X is 1-carboxymethyltetrazol-5-ylthio, and COB is carboxy;
(31) R is tolyl, X is thiadiazol-5-ylthio, and COB is carboxy;
(32) R is tolyl, X is methylthiadiazolylthio, and COB is carboxy;
(33) R is tolyl, X is triazol-4-ylthio, and COB is carboxy;
(34) R is tolyl, X is 1-methyl-5-hydroxy-6-oxo-1,6-dihydro-1,3,4-triazin-2-ylthio, and COB is carboxy;
(35) R is tolyl, X is phenylsulfinyl, and COB is carboxy;
(36) R is methoxyphenyl, X is hydrogen, and COB is carboxy;
(37) R is methoxyphenyl, X is chloro, and COB is carboxy;
(38) R is methoxyphenyl, X is bromo, and COB is carboxy;
(39) R is methoxyphenyl, X is iodo, and COB is carboxy;
(40) R is methoxyphenyl, X is hydroxy, and COB is carboxy;
(41) R is methoxyphenyl, X is nitroxy, and COB is carboxy;
(42) R is methoxyphenyl, X is formyloxy, and COB is carboxy;
(43) R is methoxyphenyl, X is acetoxy, and COB is carboxy;
(44) R is methoxyphenyl, X is propionyloxy, and COB is carboxy;
(45) R is methoxyphenyl, X is methylthio, and COB is carboxy;
(46) R is methoxyphenyl, X is phenylthio, and COB is carboxy;
(47) R is methoxyphenyl, X is methyltetrazolylthio, and COB is carboxy;
(48) R is methoxyphenyl, X is 1-carboxymethyltetrazol-5-ylthio, and COB is carboxy;
(49) R is methoxyphenyl, X is thiadiazolylthio, and COB is carboxy;
(50) R is methoxyphenyl, X is methylthiadiazolylthio, and COB is carboxy;
(51) R is methoxyphenyl, X is triazol-4-ylthio, and COB is carboxy;
(52) R is methoxyphenyl, X is 1-methyl-5-hydroxy-6-oxo-1,6-dihydro-1,3,4-triazin-2-ylthio, and COB is carboxy;
(53) R is methoxyphenyl, X is phenylsulfinyl, and COB is carboxy;
(54) R is chlorophenyl, X is hydrogen, and COB is carboxy;
(55) R is chlorophenyl, X is chloro, and COB is carboxy;
(56) R is chlorophenyl, X is bromo, and COB is carboxy;
(57) R is chlorophenyl, X is iodo, and COB is carboxy;
(58) R is chlorophenyl, X is hydroxy, and COB is carboxy;
(59) R is chlorophenyl, X is nitroxy, and COB is carboxy;
(60) R is chlorophenyl, X is formyloxy, and COB is carboxy;
(61) R is chlorophenyl, X is acetoxy, and COB is carboxy;
(62) R is chlorophenyl, X is propylthio, and COB is carboxy;
(63) R is chlorophenyl, X is phenylthio, and COB is carboxy;
(64) R is chlorophenyl, X is methyltetrazolylthio, and COB is carboxy;
(65) R is chlorophenyl, X is 1-carboxymethyltetrazolylthio, and COB is carboxy;
(66) R is chlorophenyl, X is thiadiazolylthio, and COB is carboxy;
(67) R is chlorophenyl, X is methylthiadiazolylthio, and COB is carboxy;
(68) R is chlorophenyl, X is triazolylthio, and COB is carboxy;
(69) R is chlorophenyl, X is 1-ethyl-5-hydroxy-6-oxo-1,6-dihydro-1,3,4-triazin-2-ylthio, and COB is carboxy;
(70) R is chlorophenyl, X is phenylsulfinyl, and COB is carboxy;
(71) R is nitrophenyl, X is hydrogen, and COB is carboxy;
(72) R is nitrophenyl, X is chloro, and COB is carboxy;
(73) R is nitrophenyl, X is bromo, and COB is carboxy;
(74) R is nitrophenyl, X is bromo, and COB is carboxy;
(75) R is nitrophenyl, X is iodo, and COB is carboxy;
(76) R is nitrophenyl, X is hydroxy, and COB is carboxy;
(77) R is nitrophenyl, X is nitroxy, and COB is carboxy;
(78) R is nitrophenyl, X is formyloxy, and COB is carboxy;

(79) R is nitrophenyl, X is acetoxy, and COB is carboxy;
(80) R is nitrophenyl, X is methylthio, and COB is carboxy;
(81) R is nitrophenyl, X is phenylthio, and COB is carboxy;
(82) R is nitrophenyl, X is methyltetrazolylthio, and COB is carboxy;
(83) R is nitrophenyl, X is 1-carboxymethyltetrazolylthio, and COB is carboxy;
(84) R is nitrophenyl, X is thiadiazolylthio, and COB is carboxy;
(85) R is nitrophenyl, X is methylthiadiazolylthio, and COB is carboxy;
(86) R is nitrophenyl, X is triazolylthio, and COB is carboxy;
(87) R is nitrophenyl, X is 1-methyl-5-hydroxy-6-oxo-1,6-dihydro-1,3,4-triazin-2-ylthio, and COB is carboxy;
(88) R is nitrophenyl, X is phenylsulfinyl, and COB is carboxy;
(89) R is cyanophenyl, X is hydrogen, and COB is carboxy;
(90) R is cyanophenyl, X is chloro, and COB is carboxy;
(91) R is cyanophenyl, X is bromo, and COB is carboxy;
(92) R is cyanophenyl, X is iodo, and COB is carboxy;
(93) R is cyanophenyl, X is hydroxy, and COB is carboxy;
(94) R is cyanophenyl, X is nitroxy, and COB is carboxy;
(95) R is cyanophenyl, X is formyloxy, and COB is carboxy;
(96) R is cyanophenyl, X is acetoxy, and COB is carboxy;
(97) R is cyanophenyl, X is methylthio, and COB is carboxy;
(98) R is cyanophenyl, X is phenylthio, and COB is carboxy;
(99) R is cyanophenyl, X is methyltetrazolylthio, and COB is carboxy;
(100) R is cyanophenyl, X is 1-carboxymethyltetrazolylthio, and COB is carboxy;
(101) R is cyanophenyl, X is thiadiazolylthio, and COB is carboxy;
(102) R is cyanophenyl, X is methylthiadiazolylthio, and COB is carboxy;
(103) R is cyanophenyl, X is triazolylthio, and COB is carboxy;
(104) R is cyanophenyl, X is 1-methyl-5-hydroxy-6-oxo-1,6-dihydro-1,3,4-triazin-2-ylthio, and COB is carboxy;
(105) R is cyanophenyl, X is phenylsulfinyl, and COB is carboxy;
(106) R is benzyl, X is hydrogen, and COB is carboxy;
(107) R is benzyl, X is chloro, and COB is carboxy;
(108) R is benzyl, X is bromo, and COB is carboxy;
(109) R is benzyl, X is iodo, and COB is carboxy;
(110) R is benzyl, X is hydroxy, and COB is carboxy;
(111) R is benzyl, X is nitroxy, and COB is carboxy;
(112) R is benzyl, X is formyloxy, and COB is carboxy;
(113) R is benzyl, X is acetoxy, and COB is carboxy;
(114) R is benzyl, X is methylthio, and COB is carboxy;
(115) R is benzyl, X is trifluoroacetoxy, and COB is carboxy;
(116) R is benzyl, X is ethylthio, and COB is carboxy;
(117) R is benzyl, X is phenylthio, and COB is carboxy;
(118) R is benzyl, X is methyltetrazolylthio, and COB is carboxy;
(119) R is benzyl, X is 1-carboxymethyltetrazolylthio, and COB is carboxy;
(120) R is benzyl, X is thiadiazolylthio, and COB is carboxy;
(121) R is benzyl, X is methylthiadiazolylthio, and COB is carboxy;
(122) R is benzyl, X is triazolylthio, and COB is carboxy;
(123) R is benzyl, X is 1-methyl-5-hydroxy-6-oxo-1,6-dihydro-1,3,4-triazin-2-ylthio, and COB is carboxy;
(124) R is benzyl, X is phenylsulfinylthio, and COB is carboxy;
(125) R is phenoxymethyl, X is hydrogen, and COB is carboxy;
(126) R is phenoxymethyl, X is chloro, and COB is carboxy;
(127) R is phenoxymethyl, X is bromo, and COB is carboxy;
(128) R is phenoxymethyl, X is iodo, and COB is carboxy;
(129) R is phenoxymethyl, X is hydroxy, and COB is carboxy;
(130) R is phenoxymethyl, X is nitroxy, and COB is carboxy;
(131) R is pheoxymethyl, X is formyloxy, and COB is carboxy;
(132) R is phenoxymethyl, X is acetoxy, and COB is carboxy;
(133) R is phenoxymethyl, X is methanesulfonyloxy, and COB is carboxy;
(134) R is phenoxymethyl, X is methylthio, and COB is carboxy;
(135) R is phenoxymethyl, X is phenylthio, and COB is carboxy;
(136) R is phenoxymethyl, X is methyltetrazolylthio, and COB is carboxy;
(137) R is phenoxymethyl, X is carboxymethyltetrazolylthio, and COB is carboxy;
(138) R is phenoxymethyl, X is thiadiazolylthio, and COB is carboxy;
(139) R is phenoxymethyl, X is methylthiadiazolylthio, and COB is carboxy;
(140) R is phenoxymethyl, X is triazolylthio, and COB is carboxy;
(141) R is phenoxymethyl, X is 1-methyl-5-hydroxy-6-oxo-1,6-dihydro-triazin-2-ylthio, and COB is carboxy;
(142) R is phenoxymethyl, X is phenylsulfinyl, and COB is carboxy;
(145) R is methyl, X is hydrogen, and COB is carboxy;
(146) R is methyl, X is chloro, and COB is carboxy;
(147) R is methyl, X is bromo, and COB is carboxy;
(148) R is methyl, X is iodo, and COB is carboxy;
(149) R is methyl, X is hydroxy, and COB is carboxy;
(150) R is methyl, X is nitroxy, and COB is carboxy;
(151) R is methyl, X is formyloxy, and COB is carboxy;
(152) R is methyl, X is methylthio, and COB is carboxy;
(153) R is methyl, X is phenylthio, and COB is carboxy;
(154) R is methyl, X is methyltetrazolylthio, and COB is carboxy;
(155) R is methyl, X is thiadiazolylthio, and COB is carboxy;
(156) R is methyl, X is methylthiadiazolylthio, and COB is carboxy;
(157) R is methyl, X is 1-ethyl-5-hydroxy-6-oxo-1,6-dihydro-1,3,4-triazin-2-ylthio, and COB is carboxy;
(158) R is methyl, X is phenylsulfinyl, and COB is carboxy;

(159) R is isopropyl, X is chloro, and COB is carboxy;
(160) R is isopropyl, X is iodo, and COB is carboxy;
(161) R is isopropyl, X is hydroxy, and COB is carboxy;
(162) R is t-butyl, X is hydroxy, and COB is carboxy;
(163) R is t-butyl, X is chloro, and COB is carboxy; and
(164) R is t-butyl, X is iodo, and COB is carboxy, and their carboxy-protected derivatives in a form conventional ester, amide, or salt available in the chemistry of penicillins and cephalosporins as cited above.

Stereochemically different double bond isomers have been described (Wolfe: Can. J. Chem., 50, 2902 (1972); Cooper: J. Am. Chem. Soc., 92, 2575 (1970)). However, these compounds have wrong stereochemistry at ring-fusion to serve as starting materials for preparing 1-oxacephalosporins, because they give uneffective 6α-epimers as end products by the same procedures.

II. PROCESSES

PART 1. FROM EPIPENICILLIN 1-OXIDES

Compounds (I) are preparable from epipenicillin 1-oxides (II) by subjecting to ring-opening and successive recyclization according to the following reaction scheme:

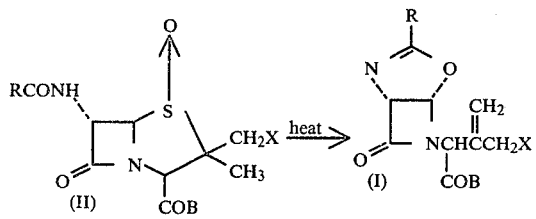

(wherein R, X, and COB are as defined above, provided the bonds S→O and C—CH₃ in Compound (II) are in cis positions)

The starting compounds (II) can be prepared by the methods analogous to those described in the Journal of the Chemical Society, Perkin I, 1973, page 932.

Said reactions can be carried out by mere heating as described in an Example below (i.e. under refluxing in a solvent of benzene and N,N-dimethylacetamide (3:2)), showing unnecessity of any reagent to be added.

The procedure runs through formation of a sulfenic acid from Compounds (II), followed by desulfurization. To the former reaction, therefore, is co-applicable a condition of processes for preparing deacetoxycephalosporanic acids from penicillin 1-oxides, and the latter is accelerated by addition of a desulfurizing reagent. The said desulfurizing reagent can be a trivalent phosphorus compound (e.g. a triarylphosphine including triphenylphosphine, tritolylphosphine, trialkylphosphine including triethylphosphine, tributylphosphine, tricyanoethylphosphine, trialkyl phosphite including trimethyl phosphite, triethyl phosphite, and phosphorus trichloride), sulfur compound (e.g. a sulfenic acid, sulfinic acid, sulfite), halo compound (e.g. a molecular halogen, N-haloacetamide, N-halosuccinimide, N-halophthalimide), acid (e.g. organic or inorganic acid), acid anhydride, or other compounds having sufficient affinity to the sulfur atom.

Water is formed during the reaction, and it is preferably removed under addition of Molecular Sieves to the reaction mixture or by azeotropical drying of the refluxing mixture. However, said drying is not indispensable in the reaction.

This reaction is preferably carried out in a solvent. Typical solvents include hydrocarbon (e.g. benzene, toluene, pentane, hexane, cyclohexane), halohydrocarbon (e.g. chloromethane, dichloromethane, chloroform, dichloroethane, trichloroethane, carbon tetrachloride, chlorobenzene), ether (e.g. diethyl ether, carbitol, diglyme, dioxane, tetrahydrofuran), amide (e.g. dimethylformamide, dimethylacetamide, hexamethylphosphorotriamide), ester (e.g. ethyl acetate, isopropyl acetate, butyl acetate, anyl acetate, methyl benzoate, alcohol (e.g. methanol, ethanol, butanol, t-butanol, pentanol), and other inert solvent.

The reaction temperature can be preferably at from 50° C. to 130° C. The reaction proceeds slowly at a temperature lower than 70° C., and with more formation of degraded product at a temperature higher than 120° C. The reaction completes within several minutes at a higher temperature and within several hours at a lower temperature.

In a typical treatment, one part by weight of the starting material is dissolved in a mixture of 7 to 15 parts by volume of a hydrocarbon solvent (e.g. benzene, toluene) and 7 to 15 parts by volume of a halohydrocarbon solvent (e.g. dichloroethane, trichloroethane), and then mixed with 0.5 to 2 mole equivalents (preferably 1.0 to 1.5 mole equivalents) of a desulfurizing reagent (preferably trimethyl phosphite or triphenylphosphine) and 1 to 5 parts by weight (especially 1.5 to 4 weights) of Molecular Sieves, and the resulted mixture is heated under reflux for 10 minutes to 15 hours (2 to 5 hours in most cases), if required, under azeotropic separation of water. Same condition gives thiazolinoazetidines from penicillin oxides.

The compounds thus prepared can be worked up, isolated, and purified by conventional methods e.g. filtering off the used Molecular Sieves, washing with water, drying, concentration, fractional crystallization, and optional purification by chromatography.

The compounds (I) thus prepared can be treated with a base to give the corresponding conjugated compound (III) according to the following scheme:

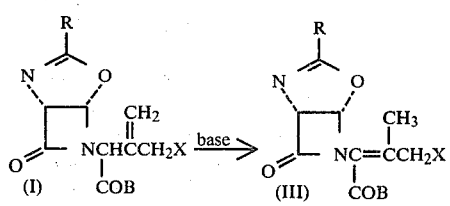

(wherein R, COB, and X are as defined above).

This reaction can also be carried out in an inert solvent in the presence of organic amine (e.g. trimethylamine, triethylamine, propyldimethylamine, N,N-dimethylaniline, pyridine, quinoline) or inorganic base (e.g. hydroxide or carbonate of an alkali metal) at e.g. 0° C. to 70° C. for 1 minute to 5 hours.

When R is an aryl in Compounds (I) and preferable to this reaction, it sometimes favors the reconversion of the compounds (III) to give further intermediates directed to the objective 1-oxadethiacephalosporins as described hereunder.

PART 2. HALOGENATION AT METHYL

As an alternative aspect, this invention includes an optional halogenation on Compound (I) or (III) where X is hydrogen to be transformed into halogen as shown in following scheme to give Compound (I') or (III'):

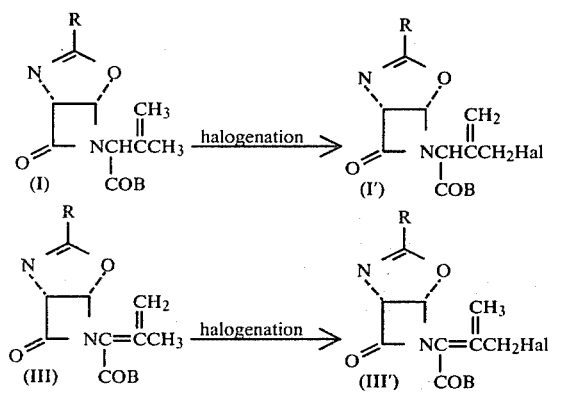

(wherein R and COB are as defined above, and Hal is a halogen).

The halogenating reagents are those capable of introducing a halogen at an allylic terminal. Representatives of them include molecular halogens (e.g. chlorine, bromine, iodine, iodine chloride, bromine chloride), sulfur halides, hypohalites (e.g. t-butyl hypohalite), copper halides (e.g. copper bromide), selenium halides (e.g. selenium oxyhalide, phenylselenium halide, selenium tetrachloride), sulfuryl halides, thionyl halides, N-haloamides, N-haloimides (e.g. N-bromosuccinimide, N-chlorosuccinimide, N-bromoacetamide, N-chloroacetamide, N-chlorophthalimide, Chloramine T, Chloramine B), N-haloisocyanuric acids, arylsulfenyl halides (e.g. phenylsulfenyl halides, benzothiazol-2-ylsulfenyl halides, quinoline-2-sulfenyl halides, o-nitrophenylsulfenyl halides, iodobenzene dichloride, pyridine hydrohalides perhalides, and like halogenating reagents. In these reagents, preferable halogen is chlorine or bromine, although iodine may also be available.

The reaction is preferably carried out in an inert solvent. Typical solvents include hydrocarbon, halohydrocarbon, carbon disulfide, ether, ester, amide, and alcohol solvents as given in Part 1, and nitrile (e.g. acetonitrile, benzonitrile), carboxylic acid (e.g. formic acid, acetic acid), base (e.g. pyridine, quinoline), water, and other inert solvents or mixtures thereof.

If required, a radical initiator (e.g. peroxides, peracids, azobisisobutyronitrile), light irradiation, hydrogen halide scavenger (e.g. pyridine, triethylamine, urea, alkaline earth metal oxides, ethylene oxide, propylene oxide, cyclohexene oxide, or like reagents) can be used for accelerating the reaction.

The reaction temperature is generally at −20° C. to 100° C. and preferably from 20° C. to 80° C.; and the reaction ends usually within 30 minutes to 24 hours, but these values vary with the choice of starting materials, reagents, concentrations, solvents, and accelerators.

In a preferable example, the starting material (I) or (III) (1 part) is treated with a halogenating reagent (1.0 to 2.0 mole equivalents) in a solvent (5 to 50 volumes by weight), usually under heating at 80° C. to 100° C. for N-haloamide halogenation or −20° C. to 30° C. for molecular halogen halogenation, if necessary, under inert gas (e.g. nitrogen, argon), and optionally in the presence of a radical initiator, hydrogen halide scavenger, or under irradiation, to give the desired halogenated compounds.

PART 3. NUCLEOPHILIC SUBSTITUTION

The compounds (I) or (III) can also be prepared from related compounds (I'') or (III'') by substitution of the Y group with another nucleophilic group X according to the following scheme:

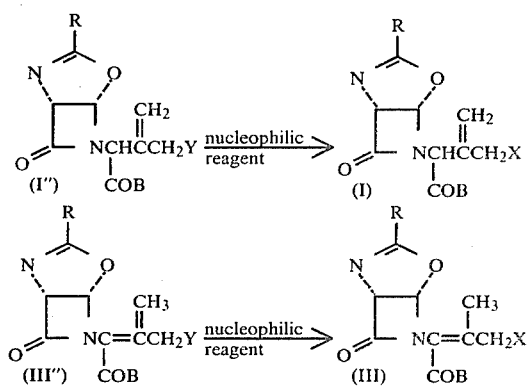

(wherein R, COB, and X are as defined above and Y is a leaving group replaceable by X)

This reaction can be carried out in a solvent as cited in Parts 1 and 2 by bringing a Compound (I) or (III) where X is Y to contact with a nucleophilic reagent. Typical reagent include an alkali metal salt (e.g. lithium, sodium, or potassium salt), heavy metal salt (e.g. silver, mercury, lead, or copper salt), organic base salt (e.g. trimethylamine or 1,1,3,3-tetramethylguanidine salt), and quarternary ammonium salt (e.g. tetraethylammonium, trimethylbenzylammonium, or methyltriphenylphosphonium salt) of a carboxylic acid (e.g. formic acid, acetic acid, propionic acid, pivalic acid, benzoic acid), mercaptan (e.g. phenyl mercaptan, 1-methyltetrazol-5-mercaptan, 2-methyl-1,3,4-thiadiazol-5-mercaptan, 1,3,4-thiadiazol-5-mercaptan, 1,2,3-triazol-4-mercaptan, 1-methyl-4-hydroxy-5-oxo-1,6-dihydro-1,3,4-triazin-2-mercaptan), sulfenic acid (e.g. phenylsulfenic acid), hydrogen halide, or like acid represented by HX wherein X is as defined above.

The reaction can be accelerated with a crown ether (e.g. dibenzo-18-crown-6-ether, cyclohexyl-18-crown-6-ether), or a phase transfer catalyst (e.g. tetrabutylammonium bromide) for increasing the anion activity.

The solvent can be the same described in Part 1 or 2. Among them, preferable ones include a polar solvent promoting ionic reactions (e.g. alcohol, amide, sulfoxide, ketone, nitrile, or nitrohydrocarbon solvents or various aqueous solvents).

The reaction can be done at room temperature, under cooling or heating, and, if required, under inert gas or with stirring. Irradiation may also be used for promoting the reaction.

The product thus prepared can be obtained by purifying e.g. concentration, extraction, washing, or other conventional methods to remove solvents, unreacted starting materials and by-products, followed by purifying in the conventional methods e.g. reprecipitation, chromatography, recrystallization, or the like.

PART 4. MISCELLANEOUS MODIFICATIONS OF X

The products (I) or (III) can be, if required, converted to compounds within or beyond the definition of formula (I) or (III) by subjecting to e.g. hydrolysis with an acid or base, oxidation with an oxidizing reagent including peroxides, treatment with a reducing reagent, e.g. sodium borohydride or triphenylphosphine, or rearrangement with heat, acid, or base, or the like reactions. For example, (1) a compound where X is acyloxy can be hydrolyzed to give a corresponding compound where X is hydroxy;

(2) a compound where X is phenylsulfenyl can be treated with an oxidizing reagent, e.g. peracid, to give a compound where X is phenylsulfinyl, followed by rearrangement under heating to give a compound where X is phenylsulfenyloxy, and then by reduction to give a compound where X is hydroxy;

(3) a compound where X is chlorine or bromine is treated with sodium iodide to give an iodo compound, followed by the treatment with heavy metal salts (e.g. silver nitrate, trifluoroacetate, copper acetate, lead acetate, copper nitrate), alkali metal perchlorate, thio compounds (e.g. thiourea, alkylthiourea) to give a Compound where X is hydroxy or acyloxy including organic or inorganic acyloxy already cited under the title of Compounds: followed by hydrolysis to remove acyl group giving a corresponding hydroxy compound.

In the course of above reactions, the double bond migration or isomerization takes place occasionally. These cases are also included in the scope of this invention. cl III. USES The Compounds (III) are treated stepwise with propargyl alcohols, hydrated, cleaved with ozone at the side chain bound at position 1, reduced, substituted with halogen, treated with triphenylphosphine to form a Wittig reagent, and then recycled to give antibacterial 1-oxodethiacephalosporins (Journal of the American Chemical Society, 96, 7582 (1974)) according to the following scheme:

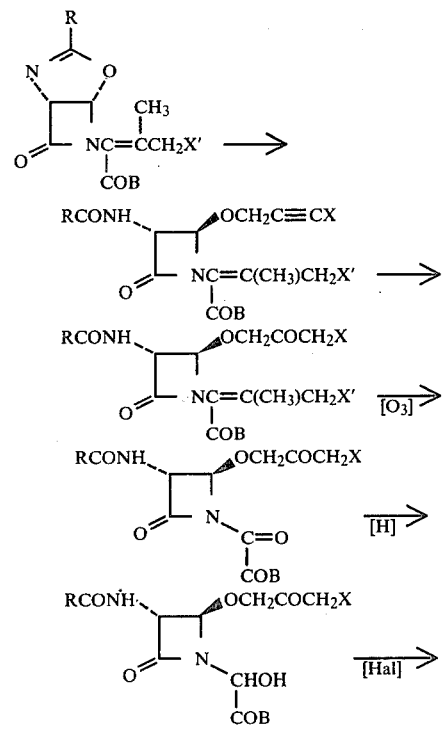

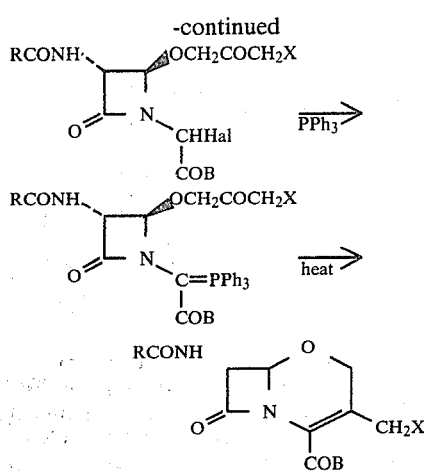

(wherein R, COB, X, and Hal are as defined above, X' is X, and Ph is phenyl).

According to this method, the objective 1-oxadethiacephalosporins are prepared in high yield because of less formation of 6-epioxadethiacephem compounds in the reaction mixture than in the known methods accompanying about 50 to 30 pecent of the undersirable epimer, and because of formation of less amount of other by-products than in the methods described in Japanese Patent Application, Open-to-Public Inspection No. 135800/1976.

In another method of use, Compound (I) where R is phenyl, COB is diphenylmethoxycarbonyl, and X is hydrogen (12 parts) is treated with osmium tetroxide (1 part) and potassium chlorate (12 parts) in a mixture of tetrahydrofuran (400 parts) and water (200 parts) is stirred at about 60° C. for 3.5 hours, poured into water, and extracted to give the corresponding vicinal diol (12.8 parts). The diol (10.9 parts) in ether (300 parts) is mixed with boron trifluoride etherate (0.075) and stirred at room temperature for 3.5 hours to give 3ξ-hydroxy-3ξ-methyl-1-oxadethiacepham compound (15 parts) after extraction with ethyl acetate and washing with water. This cepham compound (15 parts) in methylene chloride (100 parts) is mixed with pyridine (6.8 parts) and thionyl chloride (3 parts) at about 0° C., stirred for about 2 to 3 hours to give the objective 1-oxadethia-3-cephem compound which is methoxylated to give the corresponding 7α-methoxy compound as is given below:

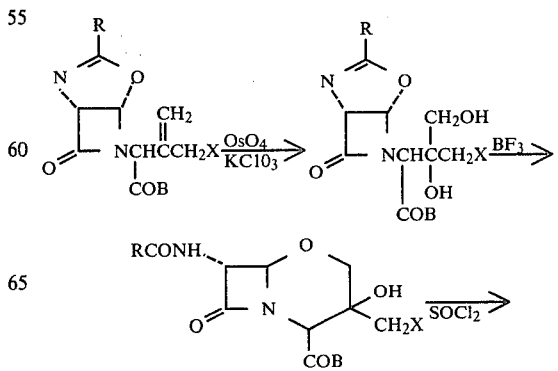

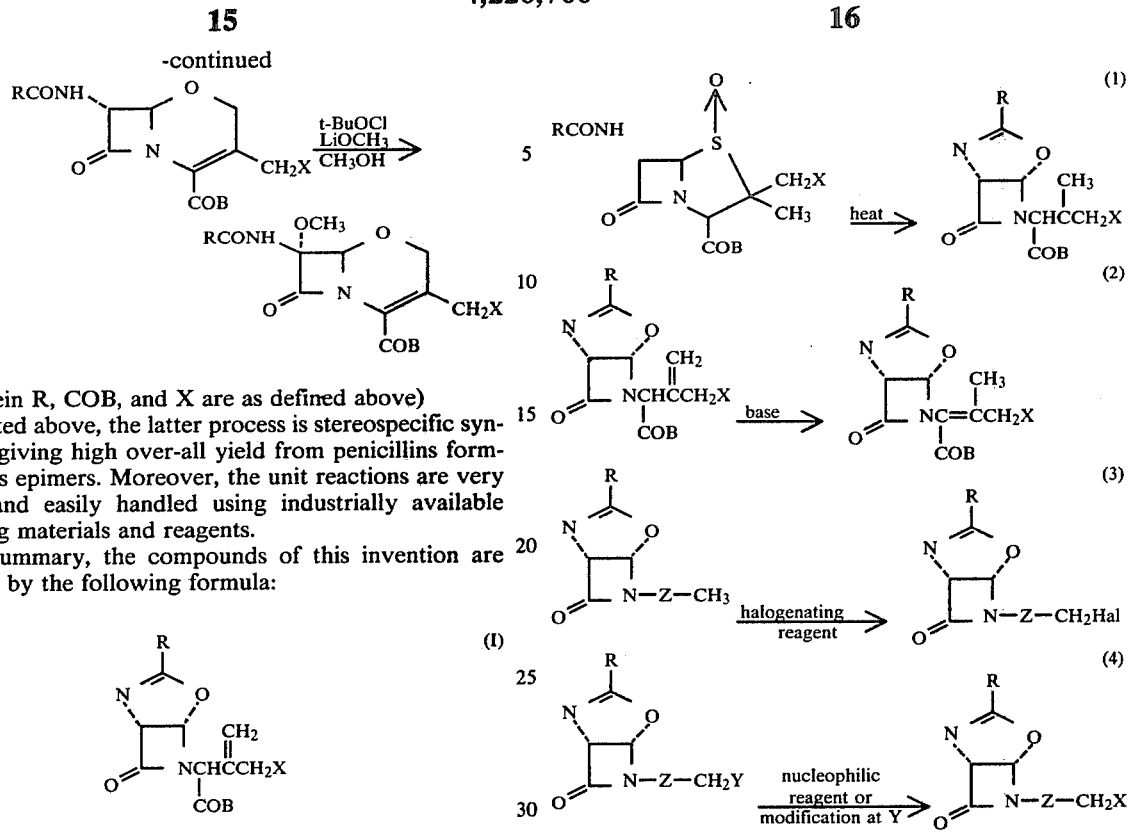

(wherein R, COB, and X are as defined above)
As stated above, the latter process is stereospecific synthesis giving high over-all yield from penicillins forming less epimers. Moreover, the unit reactions are very mild and easily handled using industrially available starting materials and reagents.

In summary, the compounds of this invention are shown by the following formula:

(I)

(wherein R, COB, and X are as defined above)
and the reactions of this invention are represented by the following shceme:

(wherein R, COB, Hal, X, and Y are as defined above and Z is a group of the formula

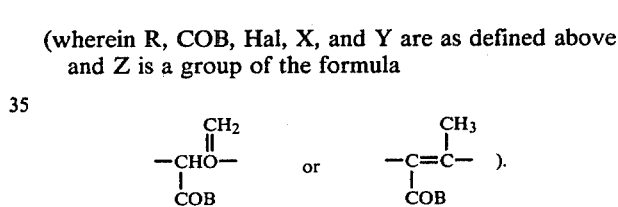

).

PREPARATION 1

Preparation of the starting material (Part 1).

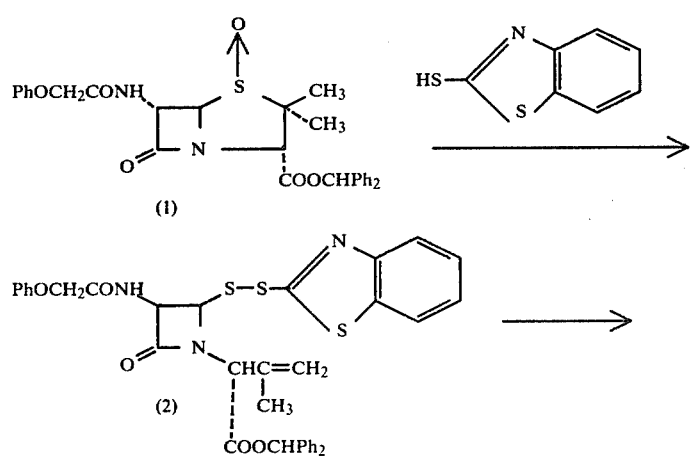

-continued

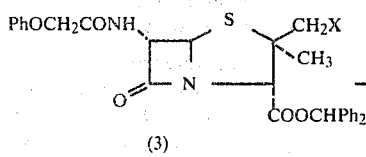 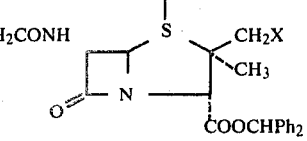

X=CH₃COO—
X=Cl—

(A) A solution of 3.63 g of Compound (1) and 1.14 g of 2-mercaptobenzothiazol in toluene is refluxed for 45 minutes and concentrated. The residue is dissolved in a small amount of methylene chloride and diluted with petroleum ether to crystallize 2.90 g of Compound (2), mp. 83°–86° C.

IR: $\nu_{max}^{CHCl_3}$ 3430, 3005, 1785, 1745, 1700 cm$^{-1}$.

NMR: $\delta^{CDCl_3}$ 1.92 brs 3H, 4.47 s2H, 5.01 s 1H, 4.9–5.3 m 3H, 5.17 d (2 Hz)1H, 6.93 s 1H, 6.8–8.1 m 15H.

(B) A solution of 1.36 g of Compound (2), 400 mg of silver acetate, and 1 ml of acetic acid in 21 ml of ethyl acetate is stirred at room temperature for 3 hours, and insoluble material is filtered off. The filtrate is concentrated, and the residue is chromatographed on 15 g of silica gel deactivated with 10% water. Elution with a mixture of benzene and ethyl acetate (95:5) affords 460 mg of Compound (3) [X=CH₃COO—].

IR: $\nu_{max}^{CHCl_3}$ 3415, 3005, 1785, 1745, 1696, 1600 cm$^{-1}$.

NMR: $\delta^{CDCl_3}$ 1.21 s 3H, 2.10 s 3H, 3.84 d (11.5 Hz)1H, 4.26 d (11.5 Hz)1H, 4.53 s 2H, 4.88 s 1H, 5.23 dd (9;2 Hz)1H, 5.38 d (2 Hz)1H, 6.98 s 1H, 6.8–7.8 m 15H.

(C) To a solution of 785 mg of Compound (3) [X=CH₃COO—] in 1.4 ml of pyridine containing 20% water is added 1.4 ml of a solution of 760 mg of iodobenzene dichloride in pyridine, and the mixture stirred at room temperature for 1.5 hours and mixed with 50 ml of ethyl acetate. The insoluble material is removed, and the filtrate evaporated under reduced pressure. The residue is purified by silica gel chromatography using a mixture of benzene and ethyl acetate (1:1) as the eluting solvent to afford 409 mg of Compound (4) [X=CH₃COO—].

IR: $\nu_{max}^{CHCl_3}$ 3420, 3010, 1795, 1750, 1700, 1600 cm$^{-1}$.

NMR: $\delta^{CDCl_3}$ 1.09 s 3H, 2.13 s 3H, 4.33 brs 2H, 4.56 s 2H, 5.01 d (2.3 Hz)1H, 5.62 dd (2.3;9 Hz)1H, 6.99 s 1H, 6.9–7.7 m 15H, 7.89 d (9 Hz)1H.

(D) A solution of 6.66 g of Compound (2) and 3.33 g of cupric chloride in 100 ml of methylene chloride is stirred at room temperature for 3 hours. The insoluble material is filtered off, and the filtrate is evaporated under reduced pressure. The residue is purified by chromatography on silica gel deactivated with 10% water to yield 2.72 g of Compound (3) [X=Cl] in 50% yield.

IR: $\nu_{max}^{CHCl_3}$ 3415, 1790, 1750, 1700, 1605 cm$^{-1}$.

NMR: $\delta^{CDCl_3}$ 1.27 s 3H, 3.47 s 2H, 4.43 s 2H, 5.10 s 1H, 5.12 dd (8 Hz;1.5 Hz)1H, (E) To a solution of 2.45 g of Compound (3) [X=Cl] in 4.5 ml of pyridine containing 20% water is added 4.5 ml of a solution of 2.45 g of iodobenzene dichloride in pyridine under ice-cooling, and the mixture stirred at room temperature for 1 hour. The reaction mixture is diluted with 200 ml of ethyl acetate, and the insoluble material filtered off. The residue is chromatographed on 45 g of silica gel deactivated with 10% water. Elution with a mixture of benzene and ethyl acetate (4:1) affords 1.23 g of Compound (4) [X=Cl] in 49% yield.

IR: $\nu_{max}^{CHCl_3}$ 3415, 1795, 1755, 1700, 1600 cm$^{-1}$.

NMR: $\delta^{CDCl_3}$ 1.07 s 3H, 3.70 brs 2H, 4.47 s 2H, 4.90 brs 1H, 5.00 s 1H, 5.48 brd (8 Hz)1H, 6.97 s 1H, 6.8–7.5 ml 5H, 8.00 brd (8 Hz)1H.

Preparation 2

Preparation of Starting materials (Part 2)

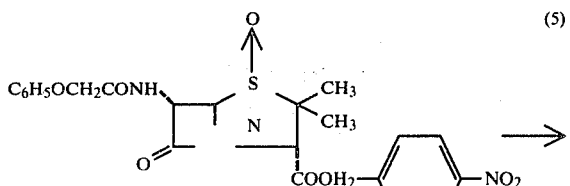

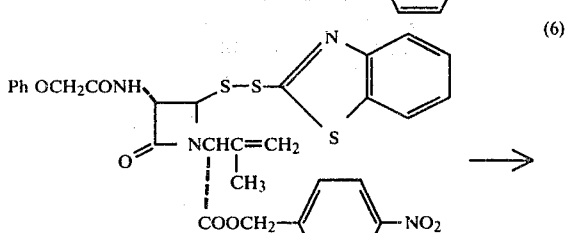

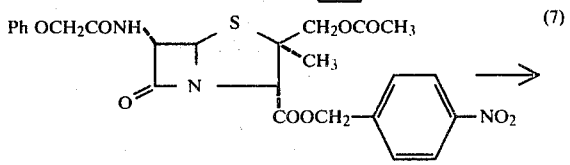

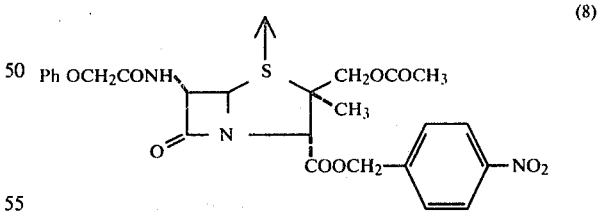

(A) In a manner similar to Preparation 1-(A), a solution of 1.02 g of Compound (5) and 0.35 g of 2-mercaptobenzothiazol in 30 ml of toluene is refluxed to yield Compound (6).

NMR: $\delta^{CDCl_3}$ 1.97 s 3H, 4.47 s 2H, 4.80–5.25 m 6H, 5.43 d (2 Hz)1H, 6.80–7.92 ml 2H, 8.10 d (8 Hz)2H. (B) The reaction mixture prepared above (A) is mixed with 5 ml of acetic acid and 0.7 g of silver acetate, and treated in a manner similar to Preparation 2-(B) to yield a mixture of 0.54 g of Compound (7) and 0.18 g p-nitrobenzyl 7α-phenoxyacetamido-3-methyl-3-acetoxycepham-4-carboxylate.

NMR: $\delta^{CDCl_3}$ 1.38 s, 1.83 s, 1.93 s, 3.43 s (3 Hz), [3.67+4.23[q (12 Hz), 4.50 s, 4.87 s, 5.30 s, 5.07–5.40 m, 6.83–7.73 m, 8.30 d (8 Hz).

(C) In a manner similar to Preparation 1-(C), a solution of 0.45 g of Compound (7) in a mixture of 2 ml of pyridine and 0.4 ml of water is mixed with 1.5 ml of a solution of 520 mg of iodobenzene dichloride in pyridine and stirred at room temperature for 3 hours to give 0.39 g of Compound (8) as foamy material.

IR: $\nu_{max}^{CHCl_3}$ 1800, 1755, 1700 cm$^{-1}$.

NMR: $\delta^{CDCl_3}$ 1.33 s 3H, 2.10 s 3H, 4.10 brs 2H, 4.57 s 2H, 4.87 s 1H, 5.05 d (2 Hz)1H, 5.33 s 2H, 5.53 dd (2;8 Hz)1H, 6.83–7.42 m 5H, [7.62+8.27]q (8 Hz)4 H, 7.93 d (8 Hz)1H.

Following examples are given to show more detailed explanation of some embodiments of this invention.

The common nucleus of Compounds (I) and (III) in the examples is shown by the following formula and named as is given below according to generally accepted nomenclature: Position numbers are also indicated for better understanding.

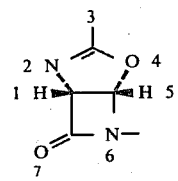

(1R,5S)-7-oxo-4-oxa-2,6-diazabicyclo[3,2,0]hept-2-ene nucleus. The stereochemistry around carbon No. 1 is identical with that in 6-epipenicillin at position 6, and that around carbon No. 5 is reverse of that in penicillins at position 5 and in cephalosporins at position 6.

Stereochemistry around α-carbon bound with COB is mainly the same with that of penicillins, but not restricted to it.

Experimental errors in IR spectra are within ±10 cm$^{-1}$, and those in NMR spectra are within ±0.2 ppm. Melting points are uncorrected.

Physical constants of the products are listed on Table IV. Ph in the chart represents a phenyl group.

PART 1. FROM 6-EPIPENICILLIN 1-OXIDES

Example I-1: Preparation of Oxazolinoazetidine compounds (I) from penicillin 1-oxides (II)

Table I shows some of the reaction conditions of the said ring-opening and successive recyclizing reactions.

The procedure of the reaction and working up in reaction No. 10 on Table I, Part 1 are illustrated below for showing details of the handling.

(No. 10)

A solution of 38.51 g of diphenylmethyl 6α-benzamidopenicillanate 1-oxide and 22.11 g of triphenylphosphine in a mixture of 308 ml of toluene and 308 ml of 1,2-dichloroethane is refluxed for 3.5 hours while removing water by means of Dean-Stark type water separator containing Molecular Sieves 5A. After cooling, the reaction mixture is concentrated to 150 ml, purified by chromatography on 500 g of silica gel deactivated with 10% water using a mixture of benzene and ethyl acetate (19:1) and then a mixture of benzene and ethyl acetate (4:1) as eluting solvents. The eluate containing the desired product is crystallized from ether to afford 28.15 g of diphenylmethyl (2R)-3-methyl-2-[(1R,5S)-3-phenyl-7-oxo-4-oxa-2,6-diazabicyclo[3,2,0-]hept-2-en-6-yl]-3-butenoate in 81.2% yield. mp. 116°–118° C.

Example I-2: Preparation of Compounds (III), the double bond isomer, from Compounds (I)

(1) To a solution of 281 mg of p-nitrobenzyl (2R)-3-methyl-2-[(1R,5S)-3-phenyl-7-oxo-4-oxa-2,6-diazabicyclo[3,2,0]-hept-2-en-6-yl]-3-butenoate in 2ml of methylene chloride is added 48 μl of triethylamine, and the mixture allowed to stand at room temperature for 15 minutes and then evaporated under reduced pressure to afford 278 mg of p-nitrobenzyl (2R)-3-methyl-2-[(1R,5S)-3-phenyl-7-oxo-4-oxa-2,6-diazabicyclo[3,2,0-]hept-2-en-6-yl]-2-butenoate as foamy material.

NMR: $\delta^{CDCl_3}$ 1.96 s 3H, 2.30 s 3H, 5.05 s 1H, 5.18 s 1H, 5.48 d (3 Hz)1H, 6.17 d (3 Hz)1H, 7.3–8.4 m.

(2) In a manner similar to the above (1), a solution of 75 mg of diphenylmethyl (2R)-3-methyl-2-[(1R,5S)-3-benzyl-7-oxo-4-oxa-2,6-diazabicyclo[3,2,0]hept-2-en-6-yl]-3-butenoate in 5 ml of methylene chloride is stirred at room temperature for 1 hour in the presence of 0.03 ml of triethylamine to afford diphenylmethyl-2-[(1R,5S)-3-benzyl-7-oxo-4-oxa-2,6-diazabicyclo[3,2,0-]hept-2-en-6-yl]-2-butenoate in 95% yield. mp. 104.5°–106° C.

PART 2. BY HALOGENATION AT METHYL

Example II-1

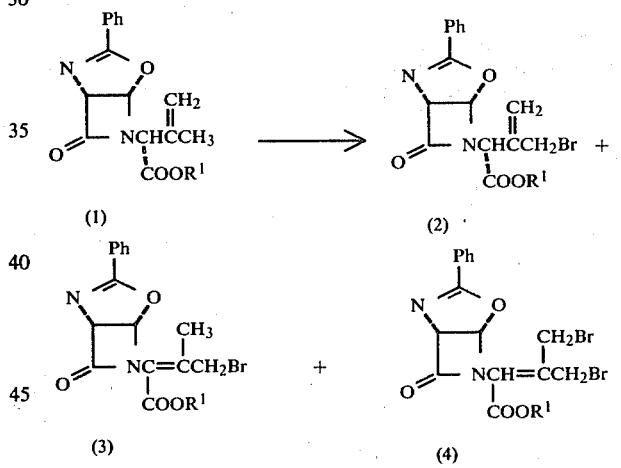

$R^1=$(a) —CHPh$_2$; (b) —CH$_3$;

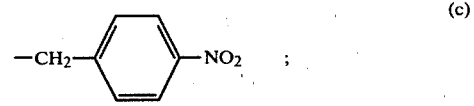

(d) —CH$_2$CCl$_3$; (e) —CH$_2$Ph (a) A suspension of 500 mg of diphenylmethyl (2R)-3-methyl-2-((1R,5S)-3-phenyl-7-oxo-4-oxa-2,6-diazabicyclo[3,2,0]hept-2-en-6-yl)-3-butenoate (1a, R$^1$=—CHPh$_2$), 238 mg of N-bromosuccinimide and 25 mg of azobisisobutyronitrile in 40 ml of carbon tetrachloride is refluxed under nitrogen atmosphere and stirred. After about 1 hour, the reaction mixture is mixed with additional 25 mg of azobisisobutyronitrile, refluxed for 30 minutes, poured into ice water, and extracted with methylene chloride. The extract is washed with water, cold aqueous sodium hydrogencarbonate solution, and water, dried over sodium sulfate, and evaporated. The residue (650 mg) shows four main spots on thin-layer chromatogram (solvent system: benzene+ethyl acetate (20:1)/silica gel plate). The residue is chromatographed on 16 g of silica gel deactivated with 10% water. Elution with a mixture (20:1) of benzene and ethyl acetate yields the products in the following order.

(1) dibromo compound (4a; $R^1$=—CHPh$_2$):23 mg, 3.5%;

(2) a mixture of monobromo compound (3a; $R^1$=—CHPh$_2$) and dibromo compound (4a; $R^1$=—CHPh$_2$): 153 mg, 23%;

(3) monobromo compound (3a; $R^1$=—CHPh$_2$): 140 mg, 26.4% (a mixture of geometrical isomers);

(4) monobromo compound (2a; $R^1$=—CHPh$_2$): 144 mg, 19%;

(5) a mixture of starting material (1a, $R^1$=—CHPh$_2$) and monobromo compound (2a): 44 mg; and (6) starting material (1a, $R^1$=—CHPh$_2$): 57 mg, 11%.

(b) In a manner similar to the above, the starting material (1b, R=—CH$_3$)(870mg) is treated with 611 mg of N-bromosuccinimide and 57 mg of azobisisobutyronitrile in 36 ml of carbon tetrachloride to yield the corresponding bromo compound, and the latter chromatographed on silica gel deactivated with 10% water. Elution with a mixture of benzene and ethyl acetate (2:1) yields the products in the following order.

(1) dibromo compound (4b, $R^1$=—CH$_3$): 144 mg, 12.3%;

(2) a mixture of dibromo compound (4b, $R^1$=—CH$_3$) and monobromo compound (3b, $R^1$=—CH$_3$): 253 mg;

(3) monobromo compound (3b, $R^1$=—CH$_3$): 95 mg, 10.3%;

(4) a mixture of two kinds of monobromo compounds (3b and 2b, $R^1$=—CH$_3$): 163 mg, (5) monobromo compound (2b, $R^1$=—CH$_3$): 325mg, 31.0%;

(6) a mixture of starting material (1b, $R^1$=—CH$_3$) and monobromo compound (2b, $R^1$=—CH$_3$): 67 mg; and (7) starting material (1b, $R^1$=—CH$_3$): 22 mg.

(c) In a manner similar to the above, the bromo compounds

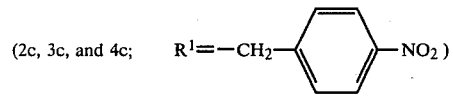

(2c, 3c, and 4c; $R^1$=—CH$_2$—⟨⟩—NO$_2$)

are obtained from the corresponding starting material

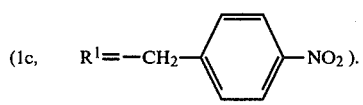

(1c, $R^1$=—CH$_2$—⟨⟩—NO$_2$).

Rf values of Compounds (4c), (3c), (2c) and (1c)

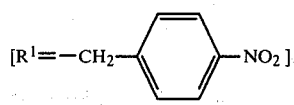

[$R^1$=—CH$_2$—⟨⟩—NO$_2$]

on thin-layer chromatography (solvent system: benzene-ethyl acetate (2:1)/silica gel plate by Merck Co.)

are about 0.49, 0.42, 0.35 and 0.31, and the quantitative ratio is about 1:2:2:1.

(d) In a manner similar to the above, to a solution of 98 mg of starting material (1d, R=—CH$_2$CCl$_3$) in 3.92 ml of carbon tetrachloride are added 91.7 mg of N-bromosuccinimide and 8.8 mg of azobisisobutyronitrile, and the mixture refluxed for 2 hours with stirring, diluted with ethyl acetate, washed with aqueous sodium thiosulfate solution, aqueous sodium hydrogencarbonate and water, dried over sodium sulfate and evaporated. The residue (110 mg) is chromatographed on Prepacked column A (by Merck Co.) which is eluted with a mixture of benzene and ethyl acetate (4:1) to yield the following products.

(1) monobromo compounds (3d, $R^1$=—CH$_2$CCl$_3$): 25 mg, 23% (a mixture (about 2:1) of geometric isomers), (2) monobromo compounds (2d, $R^1$=—CH$_2$CCl$_3$): 15 mg, 14%; and (3) starting material (1d, $R^1$=—CH$_2$CCl$_3$): 34 g, 35%.

Example II-2

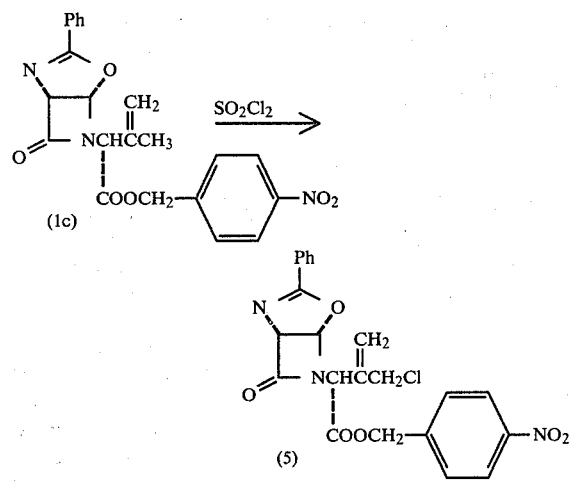

To a solution of 113 mg of p-nitrobenzyl (2R)-3-methyl-2-(1R,5S-3-phenyl-7-oxo-4-oxa-2,6-diazabicyclo[3,2,0]hept-2-en-6-yl)-3-butenoate (1c) in 2.2 ml of benzene is added 1 mg of dibenzoyl peroxide, a small amount of Molecular Sieves and 23 μl of sulfuryl chloride, and the mixture stirred at room temperature for 2.5 hours, poured into aqueous sodium hydrogencarbonate solution and extracted with ethyl acetate. The extract is washed with water, dried and evaporated. The residue is chromatographed on 5.5 g of silica gel deactivated with 10% water to yield 19 mg of p-nitrobenzyl (2R)-(1R,5S-3-phenyl-7-oxo-4-oxa-2,6-diazabicyclo-[3,2,0]hept-2-en-6-yl)-3-chloromethyl-3-butenoate.

Example II-3

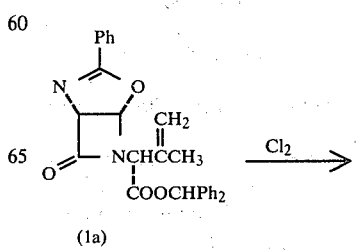

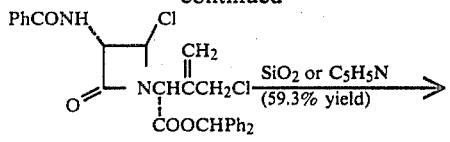

(6)

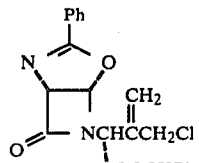

(7)

(a) To a solution of 4.525 g of diphenylmethyl (2R)-3-methyl-2-(1R,5S-3-phenyl-7-oxo-4-oxa-2,6-diazabicyclo[3,2,0]hept-2-en-6-yl)-3-butenoate (1a) in 68 ml of methylene chloride is drop-wise added 9.0 ml of 1.66 N solution of chlorine in carbon tetrachloride in a period of 30 minutes with stirring under nitrogen atmosphere. After 25 minutes, the reaction mixture is concentrated at 20° C. under reduced pressure. The residue [diphenylmethyl (2R)-2-(3α-benzamido-2-oxo-4-chloroazetidin-1-yl)-3-chloromethyl-3-butenoate (6):

NMR: $\delta^{CDCl_3}$ 4.15 d+4.45dABq(12 Hz)2H, 4.8–5.0 m 1H, 5.17 s1H, 5.50 s1H, 6.17 d(1Hz)1H, 7.00 s1H, 7.2–8.0 m15H] is chromatographed on a column of 135 g of silica gel deactivated with 10% water which is eluted with a mixture of benzene and ethyl acetate (6:1) to yield 2.888 g of diphenylmethyl (2R)-2-[(1R,5S)-3-phenyl-7-oxo-4-oxa-2,6-diazabicylo[3,2,0]hept-2-en-6-yl]-3-chloromethyl-3-butenoate (7) in 59.3% yield.

mp. 104.5°–106° C.

(b) A solution of 100 mg of Compound (1a) in ethyl acetate is reacted with a solution (2.0 molar equivalents) of chlorine in carbon tetrachloride at room temperature. The obtained product is treated with 1.2 equivalents of pyridine for 45 minutes under ice cooling, instead of chromatography of silica gel, to yield 110 mg of Compound (7).

(c) To a solution of 1 g of Compound (1a) in 30 ml of ethyl acetate is added 3.3 ml of a 1.66 N solution of chlorine in carbon tetrachloride, and the mixture reacted at room temperature for 10 minutes, treated with 0.21 ml of pyridine, and purified by chromatography on a column of silica gel to yield 454 mg of Compound (7) as main product and Compound (8) as by-product.

(d) A solution of 100 mg of Compound (1a) in 3 ml of methylene chloride is mixed with 0.2 ml of a 1.66 N solution of chlorine in carbon tetrachloride at 38° C. with stirring under nitrogen atmosphere to yield Compound (7) after silica gel chromatography.

(e) Even if the reaction is carried out at −20° C., Compound (7) is obtained.

(f) To a solution of 100 mg of Compound (1a) in 3 ml of chloroform is added 73 mg of iodobenzene dichloride under nitrogen atmosphere, and the mixture allowed to stand at room temperature overnight to yield Compound (6), and the latter treated with pyridine to yield Compound (7).

(g) If the same reaction is carried out under light irradiation, the same product (6) is obtained, but a large amount of Compound having double bound saturated with chlorine, is obtained as by-product.

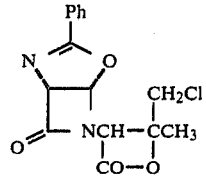

NMR: $\delta^{CD_3SOCH_3}$ (1.39 s+1.70 s)3H, [(3.82 d+4.05 d)ABq(11 Hz)+4.12 s]2H, 5.55 s 1H, [5.88 d(3 Hz)+5.65 d(3 Hz)]1H, 6.44 d (3 Hz)1H, 7.4–8.2 m 5H. IR: $\nu_{max}^{CHCl_3}$ 1845, 1790, 1635, cm$^{-1}$.

Example II-4

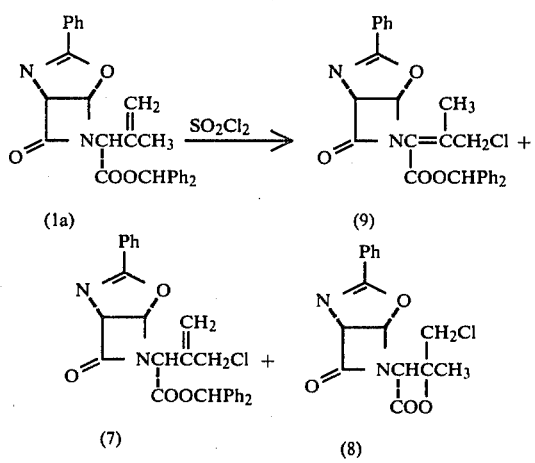

To a solution of 753 mg of Compound (1a) in 20 ml of benzene is added 1.86 g of powdered calcium oxide and 0.268 ml of sulfuryl chloride at room temperature, and the mixture stirred under nitrogen atmosphere for 1 hour. After the termination of the reaction, the insoluble matter is filtered off and the filtrate evaporated at room temperature under reduced pressure. The residue is dissolved in benzene, washed with 5% aqueous sodium hydrogencarbonate solution and water, dried over magnesium sulfate, and evaporated. The residue is chromatographed on a column of silica gel which is eluted with a mixture (4:1) of benzene and ethyl acetatre to afford 117 mg of Compound (9) in 14.5% yield, 394 mg of Compound (7) in 48.8% yield and 98 mg of Compound (8) in 18.4% yield.

Propylene oxide (10 moles), calcium oxide (0.5–20 moles), pyridine (1 mole), silica gel adsorbent, urea (the equal equivalent), and the like may be employed in the reaction as acid scavenger. Benzene and methylene chloride may be employed as solvent. When the reaction is carried out at 0° to 90° C., the termination of the reaction takes 10 to 100 minutes.

Example II-5

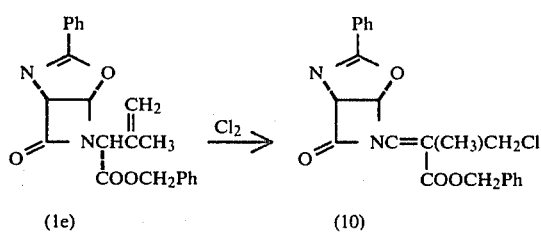

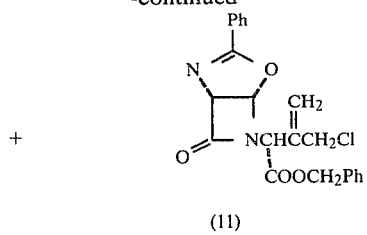

(11)

To a solution of 6.000 g of the starting material (1e, $R^1 = -CH_2Ph$) in 180 ml of ethyl acetate is dropwise added a solution (1.5 moles/L, 1.7 equivalents) of chlorine in carbon tetrachloride in a period of 21 minutes. After 15 minutes, the reaction mixture is mixed with 180 ml of a soluton of 3.53 g of sodium hydrogencarbonate and 5.90 g of sodium thiosulfate pentahydrate in water, diluted with 180 ml of acetone, stirred for 2 hours, and extracted with ethyl acetate. The extract is dried over magnesium sulfate and evaporated. The residue (7.58 g) is chromatographed on Prepacked column which is eluted with a mixture (2:1) of benzene and ethyl acetate to yield the following compounds.

(1) a mixture (1:1) of geometric isomers of Compound (10) and a mixture of the starting material and the corresponding chlorine addition product: 1.688 g (16%);

(2) Compound (11): 5.026 g (75.8%) This is crystallized from ether to yield 3.72 g of the corresponding pure product in 55.8% yield. mp. 68.5°–69° C.; and (3) The starting material, chlorohydrin compound: 82 mg.

Table II shows the other halogenations.

PART 3. BY NUCLEOPHILIC SUBSTITUTION

Example II-1

2-Oxazolinoazetidinyl-3-substituted methyl-butenoates may be prepared from 2-oxazolinoazetidinyl-3-suitably substituted methyl-butenoates on reaction with a nucleophile under the reaction conditions shown in Table III.

The procedure of reaction in No. 53 on Table III (Part 3) is illustrated below for showing detailed procedure.

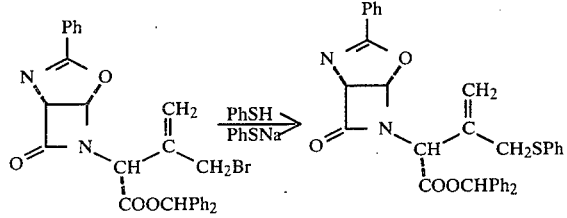

To a solution of 437 mg of diphenylmethyl (2R)-2-(3-phenyl-7-oxo-4-oxa-2,6-diazabicyclo[3,2,0]hept-2-en-6-yl)-4-bromo-3-exomethylenebutyrate in 10 ml of a mixture (3:1) of acetone and methanol are added 250 mg of phenyl mercaptan and 250 mg of sodium phenylmercaptide, and the mixture stirred at room temperature for 1 hour and at 35° C. for 1 hour, poured into water and extracted with ethyl acetate. The extract is washed with water, dried over magnesium sulfate, and evaporated. The residue is chromatographed on a column of silica gel deactivated with 10% water which is eluted with a mixture (0:1 to 1:10) of ethyl acetate and benzene to yield 400 mg of diphenylmethyl (2R)-2-(3-phenyl-7-oxo-4-oxa-2,6-diazabicyclo[3,2,0]hept-2-en6-yl)-3-phenylthiomethyl-3-butenoate in 80% yield.

IR: $\nu_{max}^{CHCl_3}$ 1787, 1755, 1636 cm$^{-1}$

PART 4. MISCELLANEOUS MODIFICATIONS

Example IV-1

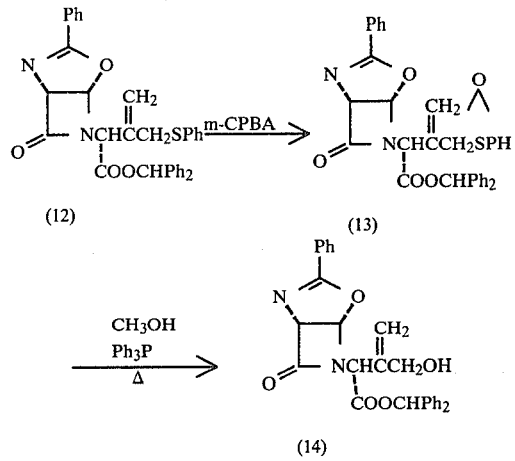

To a solution of 703 mg of Compound (12) in 14 ml of chloroform is dropwise added a solution of 220 g of m-chloroperbenzoic acid in 7 ml of chloroform, and the mixture stirred for 10 minutes, mixed with 700 mg of triphenylphosphine and 70 μl of methanol and refluxed under heating at 75° C. After the termination of the reaction, the mixture is evaporated under reduced pressure. The residue is chromatographed on a column of 30 g of silica gel deactivated with 10% water which is eluted with benzene containing 20–30% ethyl acetate and the eluate containing the desired product evaporated to yield 401 mg of Compound (14) in 68% yield.

Example IV-2

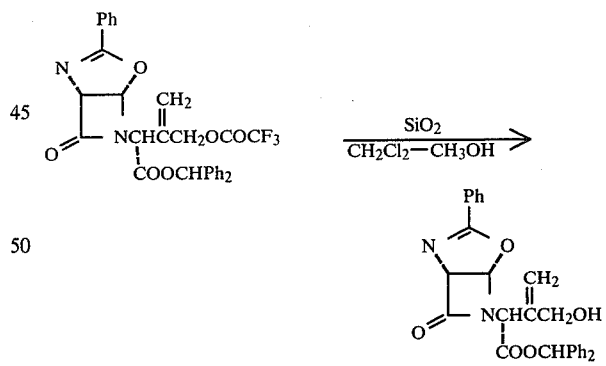

To a solution of 240 mg of diphenylmethyl (2R-2-(3-phenyl-7-oxo-4-oxa-2,6-diazabicyclo[3,2,0]hept-2-en-6-yl)-3-trifluoroacetyloxymethyl-3-butenoate in 10 ml of a mixture (4:1) of methanol and methylene chloride is added 4.8 g of silica gel containing 10% water, and the mixture stirred for 30 minutes and filtered. The filter cake, silica gel, is washed several times with a mixture of methanol and methylene chloride. The combined filtrate and washings are evaporated under reduced pressure. The oily residue is chromatographed on 12 g of silica gel. Elution with a mixture (2:1) of benzene and ethyl acetate yields 106 mg of diphenylmethyl (2R)-2-(3-phenyl-7-oxo-4-oxa-2,6-diazabicyclo[3,2,0]hept-2-en- 6-yl)-3-hydroxymethyl-3-butenoate in 53% yield and 90 mg of the starting material in 35% recovery.

Example IV-3

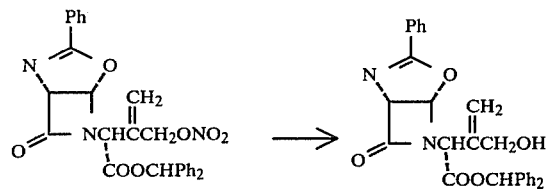

Diphenylmethyl (2R)-2-(3-phenyl-7-oxo-4-oxa-2,6-diazabicyclo[3,2,0]hept-2-en-6-yl)-3-iodomethyl-3-butenoate is reacted with calcium carbonate and silver nitrate to yield a mixture (1:3) of diphenylmethyl (2R)-2-(3-phenyl-7-oxo-4-oxa-2,6-diazabicyclo[3,2,0]hept-2-en-6yl)-3-hydroxymethyl-3-butenoate an diphenylmethyl (2R)-2-(3-phenyl-7-oxo-4-oxa-2,6-diazabicylo[3,2,0]hept-2-en-6-yl)-3-nitroxymethyl-3-butenoate andd the mixture dissolved in 4.5 ml of methylene chloride. To the solution prepared above is dropwise added 0.5 ml of acetic acid, and the mixture mixed with 300 mg of zinc, stirred at 0° C. for 15 minutes, diluted with methylene chloride, washed with water, dried, and evaporated. The residue is purified by thin-layer chromatography to yield 90 mg of diphenylmethyl (2R)-2-(3-phenyl-7-oxo-4-oxa-2,6-diazabicyclo[3,2,0]hept-2-en-6-yl)-3-hydroxymethyl-3-butenoate.

Example of the use of Compound (I)

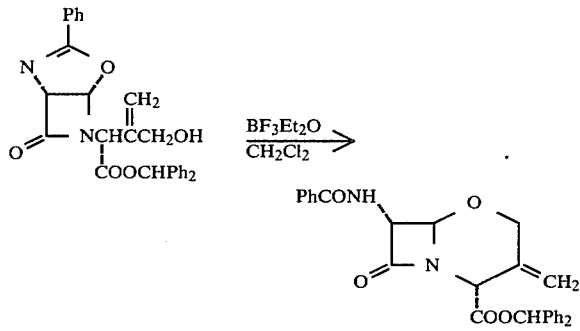

To a solution of 950 mg of crude diphenylmethyl (2R)-2-(3-phenyl-7-oxo-4-oxa-2,6-diazabicyclo[3,2,0-]hept-2-en-6-yl)-3-hydroxymethyl-3-butenoate in 15 ml of methylene chloride is added 20 μl of boron trifluoride etherate at room temperature, and the mixture stirred at the same temperature for 1.5 hours, and evaporated. The residue is chromatographed on 30 g of silica gel. Elution with a mixture (4:1) of benzene and ethyl acetate yields 0.686 g of diphenylmethyl 7α-benzoylamino-3-exomethylene-1-oxa-dethiacepham-4α-carboxylate as foamy material in 81% yield.

This is isomerized with triethylamine to give diphenylmethyl 7α-benzoylamino-3-methyl-1-oxadethia-3-cephem-4-carboxylate.

The latter is treated with t-BuOCl and LiOCH$_3$ to give diphenylmethyl 7β-benzoylamino-7α-methoxy-3-methyl-3-cephem-4-carboxylate, which is solvolyzed with trifluoroacetic acid and anisole to give the corresponding free acid.

Abbreviations in following tables are as follows:

| | |
|---|---|
| Ac | acetyl |
| An | acetone |
| aq | aqueous |
| C$_5$H$_5$N | pyridine |
| —C$_6$H$_4$— | phenylene |
| DMA | N,N-dimethylacetamide |
| DMSO | dimethyl sulfoxide |
| ds | dried with Dean-Stark type water separator |
| Et | ethyl |
| h. | hour(s) |
| i- | iso- |
| m. | minute(s) |
| on | overnight |
| Ph | phenyl |
| polymer* | a styrene-divinylbenzene copolymer containing diphenylphosphoranylphenyl group (K. Horiki, Tetrahedron Letters, 1976, 4103). |
| refl. | refluxing temperature |
| rt | room temperature |
| t- | tertiary- |
| Ts | p-CH$_3$C$_6$H$_4$SO$_2$— |

Table I (Part 1)

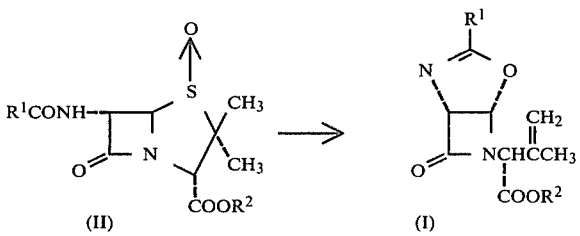

| No. | R$^1$ | R$^2$ | II (g) | Solvent (ml) | Reagent (g) | Molecular Sieves 5A (g) | Temperature (°C.) | Time (hr) |
|---|---|---|---|---|---|---|---|---|
| 1. | Ph— | —CH$_3$ | 8.39 | (CH$_2$Cl)$_2$ (150) | PPh$_3$ (8.28) | 35 | refl. | 6h. |
| 2. | " | —CH$_2$Ph | 8.53 | PhCH$_3$(85) + (CH$_2$Cl)$_2$(85) | PPh$_3$ (6.29) | 22 | " | 3h.10m. |
| 3. | " | " | 0.21 | PhH(3) + DMA(2) | HO-[ ]-O (0.06) + HO-[ ]-O C$_5$H$_5$N(0.072) | — | " | 2h. |
| 4. | " | " | 0.21 | PhH(3) + DMA(2) | — | — | " | " |
| 5. | " | " | 0.43 | DMA (5) | (CH$_3$CO)$_2$O(0.47) | — | 115 | 70m. |

Table I (Part 1)-continued

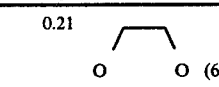

| No. | R¹ | R² | II (g) | Solvent (ml) | Reagent (g) | Molecular Sieves 5A (g) | Temperature (°C.) | Time (hr) |
|---|---|---|---|---|---|---|---|---|
| 6. | " | " | 0.21 | ⟨morpholine-like⟩ (6) | $C_5H_5N$(0.2) + 85% $H_3PO_4$(0.17) | ds | refl. | " |
| 7. | " | $-CH_2\text{-}C_6H_4\text{-}NO_2$ | 2.50 | $(CH_2Cl)_2$(100) | $PPh_3$ (1.67) | 10 | " | 4h. |
| 8. | " | " | 8.53 | $PhCH_3$(85) + $(CH_2Cl)_2$(85) | $PPh_3$ (5.70) | 20 | " | 3h.10m. |
| 9. | " | $-CHPh_2$ | 3.00 | $(CH_2Cl)_2$ (80) | $P(OCH_3)_3$ (1.41) | 10 | " | 5h. |
| 10. | " | " | 38.51 | $PhCH_3$(308) + $(CH_2Cl)_2$(308) | $PPh_3$ (22.1) | — | " | 3h.30m. |
| 11. | " | " | 5.03 | $PhCH_3$ (150) | $P(O\text{-}i\text{-}C_3H_7)_3$(2.6) | 12.5 | " | 45m. |
| 12. | " | " | 27.65 | $PhCH_3$ (611) | $PPh_3$ (17.32) | 83 | " | 55m. |
| 13. | " | " | 0.10 | $(CH_2Cl)_2$ (2) | $P(n\text{-}C_4H_9)_3$(0.1 ml) | 0.3 | " | 9h. |
| 14. | " | " | 1.58 | $(CH_2Cl)_2$ (39) | $PPh_3$(polymer*)(2.7) | ds. | " | 8.5h. |
| 15. | " | " | 5.0 | $t\text{-}C_4H_9OH$(17) + $C_2H_3Cl_3$(34) | $PPh_3$ (2.88) | 15 | " | 4h. |

Table I (Part 2)

| No. | R¹ | R² | II (g) | Solvent (ml) | Reagent (g) | Molecular Sieves 5A (g) | Temperature (°C.) | Time |
|---|---|---|---|---|---|---|---|---|
| 16. | $PhCH_2-$ | $-CH_2Ph$ | 0.2 | $(CH_2Cl)_2$ (10) | $P(OCH_3)_3$ (0.1) | ds. | refl. | 5h. |
| 17. | " | " | 0.2 | PhH(7) | $P(OCH_3)_3$ (0.1) | " | " | 5h. |
| 18. | " | $-CHPh_2$ | 1.20 | PhH (42) | $P(OCH_3)_3$ (0.6 ml) | " | " | 8h. |
| 19. | " | " | 5.0 | $(CH_2Cl)_2$ (120) | $P(OCH_3)_3$ (2.5 ml) | " | " | 7h. |
| 20. | " | " | 0.2 | $(CH_2Cl)_2$ (10) | $PPh_3$ (0.21) | " | " | 6h. |
| 21. | " | " | 0.2 | $(CH_2Cl)_2$ (10) | $P(OCH_3)_3$ (0.1) | 0.6 | " | 5h. |
| 22. | " | " | 8.53 | $PhCH_3$(85) + $(CH_2Cl)_2$(85) | $PPh_3$ (5.19) | 22 | " | 3h.10m. |
| 24. | $PhOCH_2-$ | $-CH_2Ph$ | 0.2 | PhH (7) | $P(OCH_3)_3$ (0.1 ml) | ds. | " | 5h. |
| 25. | " | " | 0.2 | $PhCH_3$ (5) | $P(OCH_3)_3$ (0.1) | ds. | " | 1h.30m. |
| 26. | " | $-CHPh_2$ | 90 | $(CH_2Cl)_2$ (900) | $PPh_3$ (91.4) | 270 | " | 10h. |
| 27. | $-CH_3$ | $-C_4H_9\text{-}t$ | 0.1 | PhH (1) | $PPh_3$ (0.1) | ds. | " | 3h. |
| 28. | $p\text{-}CH_3C_6H_4-$ | $-CHPh_2$ | 8.53 | $PhCH_3$(85) + $(CH_2Cl)_2$ (85) | $PPh_3$ (5.19) | 22 | " | 3h.10m. |
| 29. | $p\text{-}CH_3OC_6H_4-$ | " | 8.53 | $PhCH_3$(85) + $(CH_2Cl)_2$ (85) | $PPh_3$ (5.04) | 22 | " | 8h.10m. |
| 30. | $p\text{-}O_2NC_6H_4-$ | " | 8.53 | $PhCH_3$(85) + $(CH_2Cl)_2$ (85) | $PPh_3$ (4.91) | 22 | " | 5h. |
| 31. | $p\text{-}ClC_6H_4-$ | " | 8.53 | $PhCH_3$(85) + $(CH_2Cl)_2$ (85) | $PPh_3$ (5.0) | 22 | " | 4h.30m. |
| 32. | $p\text{-}NCC_6H_4-$ | " | 8.53 | $PhCH_3$(85) + $(CH_2Cl)_2$ (85) | $PPh_3$ (5.09) | 22 | " | 8h.30m. |
| 33. | $PhCH_2-$ | $-C_4H_9\text{-}t$ | 10.0 | $PhCH_3$(50) + $(CH_2Cl)_2$ (50) | $PPh_3$ (6.64) | — | " | 2h.30m. |

Table I (Part 3)

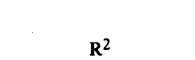

| No. | R¹ | R² | X | II (g) | Solvent (ml) | Reagent (g) | Molecular Sieves 5A (g) | Temperature (°C.) | Reaction Time |
|---|---|---|---|---|---|---|---|---|---|
| 1. | $-CH_2OPh$ | $-CH_2\text{-}C_6H_4\text{-}NO_2$ | $-OCCH_3$ (O) | 0.39 | $PhCH_3$ (5) | $P(i\text{-}C_3H_7)_3$ (0.18) | 1.2 | refl. | 40m. |
| 2. | " | $-CHPh_2$ | " | 0.24 | $PhCH_3$ (3) | $PPh_3$ (0.126) | 0.35 | " | 30m. |
| 3. | " | " | $-Cl$ | 1.06 | $PhCH_3$ (30) | $PPh_3$ (0.59) | 3.3 | " | 10m. |

Table I (Part 4)

To a solution of Compound I having the following figures (1 weight) in 1,2-dichloroethane (10 v/w) is added triphenylphosphine (1.2 mole equivalents against Compound I) and Molecular Sieves (2.5 weights) and the mixture is heated under reflux until maximum formation of the product (4 to 10 hours). The reaction mixture is worked up as in No. 10 on Table I, Part 1, to give the corresponding Compound II having the same figures in the following table.

| No. | R¹ | R² | X |
|---|---|---|---|
| 1 | —Ph | —H | —H |
| 2 | " | —CH₃ | —Br |
| 3 | " | —CH₂CCl₃ | " |
| 4 | " | —CH₂Ph | —Cl |
| 5 | " | " | —Br |
| 6 | " | " | —I |
| 7 | " | " | —OH |
| 8 | " | —CH₂—C₆H₄—NO₂ | —Cl |
| 9 | " | " | —Br |
| 10 | " | —CHPh₂ | —Cl |
| 11 | " | " | —Br |
| 12 | " | " | —I |
| 13 | " | " | —OH |
| 14 | " | " | —OC(O)CF₃ |
| 15 | " | " | —S—C(NHCH₃)=N—N=N (methylaminothiatriazole) |
| 16 | —Ph | —CHPh₂ | —SPh |
| 17 | " | " | —SC₆H₄CH₃-p |
| 18 | —CH₂Ph | —C₄H₉-t | —Cl |
| 19 | " | " | —I |
| 20 | " | " | —OH |
| 21 | " | " | —OCH₃ |
| 22 | " | —CH₂Ph | —Cl |
| 23 | " | " | —I |
| 24 | " | " | —OH |
| 25 | " | —CHPh₂ | —Cl |
| 26 | " | " | —I |
| 27 | " | " | —OH |
| 28 | " | " | —OCH₃ |
| 29 | —CH₂Ph | —CHPh₂ | —OH |
| 30 | " | " | —OCHO |
| 31 | —C₆H₄CH₃-p | —CHPh₂ | —Cl |
| 32 | " | " | —I |
| 33 | " | " | —OH |
| 34 | —C₆H₄NO₂-p | " | —Cl |
| 35 | " | " | —I |
| 36 | " | " | —OH |
| 37 | —C₆H₄CN-p | " | —Cl |
| 38 | " | " | —I |
| 39 | " | " | —OH |
| 40 | —C₆H₄Cl-p | " | —Cl |
| 41 | " | " | —I |
| 42 | " | " | —OH |

TABLE II $$\underset{(Ia)}{\overset{R^1}{\underset{O}{\bigg\langle}}\!\!\!\overset{\phantom{O}}{\underset{N}{\bigg\rangle}}\!\!\!\overset{CH_2}{\underset{\substack{|\\COOR^2}}{\text{NCHCCH}_2Y}}} \longrightarrow \underset{(I)}{\overset{R^1}{\underset{O}{\bigg\langle}}\!\!\!\overset{\phantom{O}}{\underset{N}{\bigg\rangle}}\!\!\!\overset{CH_2}{\underset{\substack{|\\COOR^2}}{\text{NCHCCH}_2X}}}$$

| No. | R¹ | R² | Y | X | Ia (g) | Solvent/Reagent (ml or g(underlined)) | Temp(°C.) Time(hr) | Solvent/Reagent (ml or g(underlined)) | Temp(°C.) Time(hr) | Yield (g) | (°C.) |
|---|---|---|---|---|---|---|---|---|---|---|---|
| 1 | —CH₂Ph | —C₄H₉-t | —H | —Cl | 1.0 | EtOAc(50)1.83M HCl/EtOAc(1.6) 1.43M Cl₂/CCl₄(3.9)CaO(0.3) | −20 2/3 | An(40)H₂O(20)NaHCO₃(0.7) Na₂S₂O₃·5H₂O(0.07) | rt 2 | 0.49 | 45 |
| 2 | " | —CH₂Ph | " | " | 1.0 | EtOAc(50)2.58M HCl/EtOAc(2.7) SO₂Cl₂(0.31) | −20 5/4 | An(12)H₂O(9) 1N NaHCO₃(7.7)aq | rt 4.25 | 0.49 | 53 |
| 3 | " | " | " | " | 1.0 | EtOAc(25)2.38M HCl/AcOEt(0.6) 1.28M Cl₂/CCl₄(2) | −20 1/2 | An(6)AcOEt(12)H₂O(4.5) 1N NaHCO₃(3.8)aq | rt 4 | 0.27 | 50 |
| 4 | " | —CHPh₂ | " | " | 4.6 | EtOAc(70)2.74M HCl/AcOEt(3.8) 1.74M Cl₂/CCl₄(12) | rt 1/4 | An(240)NaHCO₃(3.4) 5%Na₂S₂O₃(80) | rt 2.5 | 3.33 | 67 |
| 5 | —C₆H₄CH₃-p | " | " | " | 3.2 | EtOAc(195) 1.2M Cl₂/CCl₄(11.7) | 20 1/2 | 0.61M ZnCl₂/Et₂O(1.14) CaO(0.78) | rt 1.5 | 2.10 | 60 |
| 6 | —C₆H₄NO₂-p | " | " | " | 1.0 | EtOAc(60) 1.2M Cl₂/CCl₄(3.3) | 20 1/2 | 0.61M ZnCl₂/Et₂O(0.4) CaO(0.23) | 20 2.5 | 0.60 | 56 |
| 7 | —C₆H₄CN-p | " | " | " | 1.0 | EtOAc(60) 1.2M Cl₂/CCl₄(3.5) | 15 1/2 | 1.6M ZnCl₂/Et₂O(0.34) CaO(0.32) | 18 1.5 | 0.62 | — |
| 8 | —C₆H₄Cl-p | " | " | " | 1.0 | EtOAc(60) 1.2M Cl₂/CCl₄(3.5) | 15 1/2 | 1.6M ZnCl₂/Et₂O(0.34) CaO(0.32) | 18 1.5 | 0.58 | — |
| 9 | —CH₂OPh | " | " | " | 2.5 | EtOAc(74)2.58M Ac(74)2.58M HCl/Et₂O(2.18) 1.36M Cl₂/CCl₄(5.6) | 0 1/6 | An(74)H₂O(74)NaHCO₃(1.15) Na₂S₂O₃5H₂O(2.54) | 0 5 | 1.66 | 63 |

TABLE III (Part 1)

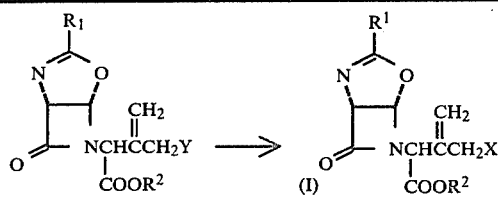

| No. | $R^1$ | $R^2$ | Y | X | Ia (g) | Solvent (ml) | Reagent (g) | Temp (°C.) | Time (hr) | Yield (g) | Yield (%) |
|---|---|---|---|---|---|---|---|---|---|---|---|
| 1 | —Ph | —CHPh$_2$ | —Cl | —I | 4.0 | An(30) | NaI(4.0) | rt | 2 | 4.67 | 98 |
| 2 | " | —CH$_2$Ph | " | " | 1.0 | An(8) | NaI(1.01) | rt | 2.5 | 1.18 | 96.6 |
| 3 | " | —CHPh$_2$ | " | " | 0.10 | AcOEt(5)H$_2$O (0.062) | NaI(0.12)Na$_2$S$_2$O$_3$5H$_2$O(0.01) (C$_4$H$_9$)$_4$NBr(0.033) | rt | 5 | — | 100 |
| 4 | " | " | " | " | 0.20 | CH$_3$COCH(CH$_3$)$_2$(2) | NaI(0.2) | rt | 1 | — | 100 |
| 5 | " | " | " | " | 0.20 | CS$_2$ | NaI(0.12)ZnCl$_2$(0.02) | rt | on | — | 50 |
| 6 | —CH$_2$Ph | " | " | " | 4.40 | An(20) | NaI(3.6)Na$_2$S$_2$O$_3$5H$_2$O(0.5) | rt | 7/4 | 3.54 | 68 |
| 7 | " | —CH$_2$Ph | " | " | 10 | An(100) | NaI(10.6)Na$_2$S$_2$O$_3$5H$_2$O(0.58) | 10 | 3 | — | 89 |
| 8 | " | —C$_4$H$_9$-t | " | " | 0.43 | An(8) | NaI(0.49)Na$_2$S$_2$O$_3$5H$_2$O(0.03) | rt | 2 | 0.51 | 97 |
| 9 | —C$_6$H$_4$CH$_3$-p | —CHPh$_2$ | " | " | 1.9 | An(20) | NaI(1.7)Na$_2$S$_2$O$_3$5H$_2$O(0.1) | rt | 2.5 | 2.22 | 99 |
| 10 | —C$_6$H$_4$NO$_2$-p | " | " | " | 0.49 | An(10) | NaI(0.41)Na$_2$S$_2$O$_3$5H$_2$O(0.02) | rt | 2.5 | 0.57 | 99 |
| 11 | —C$_6$H$_4$CN-p | " | " | " | 0.50 | An(6) | NaI(0.5) | rt | 2 | 0.43 | — |
| 12 | —C$_6$H$_4$Cl-p | " | " | " | 0.45 | An(6) | NaI(0.45) | rt | 2 | 0.45 | — |
| 13 | —Ph | " | " | —OH | 0.20 | DMSO(7)H$_2$O(3) | NaI(0.4)CaCO$_3$(0.20) | 45 | 16 | 0.07 | 39 |
| 14 | " | —CH$_2$Ph | —I | " | 0.7 | An(8)H$_2$O(3) | AgClO$_4$(0.434)CaCO$_3$(0.21) | rt | 5 | — | — |
| 15 | " | —CHPh$_2$ | " | " | 1.0 | An(30) | AgClO$_4$(0.54)CaCO$_3$(0.26) | rt | 5 | 0.95 | — |
| 16 | " | " | " | " | 0.56 | DMSO(10)H$_2$O(3.5) | CaCO$_3$ | 60 | 3 | 0.30 | 63 |
| 17 | " | " | " | " | 0.05 | DMSO(1.5) | pH 5 Buffer(0.5) | 70 | 1.5 | — | 50 |
| 18 | " | " | " | " | 0.05 | DMSO(1.5)H$_2$O(0.5) | BaCO$_3$(0.05) | 65 | 3 | — | 60 |
| 19 | " | " | " | " | 0.05 | DMSO(1.5)H$_2$O(0.5) | SrCO$_3$(0.05) | 65 | 3 | — | 60 |
| 20 | " | " | " | " | 0.30 | An(6)H$_2$O(2) | AgBF$_4$(0.13)CaCO$_3$(0.06) | rt | 3 | — | 87 |

TABLE III (Part 2)

$$\underset{(Ia)}{\overset{R^1}{\underset{N}{\bigvee}}\overset{O}{\underset{}{\bigvee}}\overset{CH_2}{\underset{COOR^2}{\underset{|}{NCHCCH_2Y}}}} \longrightarrow \underset{(I)}{\overset{R^1}{\underset{N}{\bigvee}}\overset{O}{\underset{}{\bigvee}}\overset{CH_2}{\underset{COOR^2}{\underset{|}{NCHCH_2X}}}}$$

| No. | $R^1$ | $R^2$ | Y | X | Ia (g) | Solvent (ml) | Reagent (g) | Temp (°C.) | Time (hr) | Yield (g) | (%) |
|---|---|---|---|---|---|---|---|---|---|---|---|
| 21 | —Ph | —CHPh$_2$ | —I | —OH | 0.30 | DMSO(3)H$_2$O(1) | AgNO$_3$(0.11)CaCO$_3$(0.06) | rt | 1/4 | — | 79 |
| 22 | " | " | " | " | 0.20 | DMSO(2)H$_2$O(0.5) | Cu(0.1)CaCO$_3$(0.06) | 50 | 2.5 | — | 50 |
| 23 | " | " | " | " | 0.20 | DMSO(2)H$_2$O(0.59) | ZnO(0.09) | 50 | 2 | — | 50 |
| 24 | " | " | " | " | 0.20 | DMSO(2)H$_2$O(0.5) | MgO(0.04) | 50 | 2 | — | 30 |
| 25 | " | " | " | " | 0.20 | DMSO(4)H$_2$O(1) | Ag$_2$O(0.138) | rt | 1/4 | — | 50 |
| 26 | " | " | " | " | 0.20 | An(4)H$_2$O(1) | Cu$_2$O(0.1) | 60 | 10 | — | 50 |
| 27 | " | " | " | " | 0.20 | DMSO(2)H$_2$O(0.5) | CoCO$_3$ . Co(OH)$_2$(0.12) | 50 | 7 | — | 90 |
| 28 | " | " | " | " | 0.20 | DMSO(2)H$_2$O(0.5) | CuI(0.07)CaCO$_3$(0.07) | 50 | 3 | 0.15 | 90 |
| 29 | " | " | —Cl | " | 0.20 | DMSO(4)H$_2$O(1) | CuI(0.16)NaI(0.18)CaCO$_3$(0.08) | 50 | 7 | — | 50 |
| 30 | —CH$_2$Ph | —C$_4$H$_9$-t | —I | " | 0.5 | DMSO(5)H$_2$O(1) | Cu$_2$O(0.3) | 40 | 2 | 0.22 | 57 |
| 31 | " | —CH$_2$Ph | " | " | 23 | DMSO(265)H$_2$O(67) | Cu$_2$O(12.7)H$_2$O(67) | 40 | 1.5 | 6.44 | 36 |
| 32 | " | —CHPh$_2$ | " | " | 1.59 | DMSO(13)H$_2$O(3) | CuO(0.77) | 39 | 1 | 0.35 | 27 |
| 33 | —C$_6$H$_4$CH$_3$-p | " | " | " | 0.59 | DMSO(6)H$_2$O(0.6) | Cu$_2$O(0.21) | 15 | 0.75 | 0.49 | 100 |
| 34 | —C$_6$H$_4$NO$_2$-p | " | " | " | 0.50 | DMSO(4.5)H$_2$O(0.15) | Cu$_2$O(0.17) | rt | 2.5 | 0.45 | 109 |
| 35 | —C$_6$H$_4$CN-p | " | " | " | 0.23 | DMSO(2.5)H$_2$O(0.4) | Cu$_2$O(0.2) | 50 | 1.5 | 0.10 | — |
| 36 | —C$_6$H$_4$Cl-p | " | " | " | 0.20 | DMSO(2.5)H$_2$O(0.4) | Cu$_2$O(0.2) | 50 | 1 | 0.12 | — |
| 37 | —CH$_2$Ph | —C$_4$H$_9$-t | —ONO$_2$ | " | 3.1 | CH$_2$Cl$_2$(70) | Zn(4.73)CH$_3$COOH(4.13) | 0 | 0.8 | 1.37 | 51 |
| 38 | " | " | " | —OH | 0.08 | An(1.6) | Zn(0.1)CH$_3$COOH(0.087) | 0 | 1.5 | 0.33 | 45 |
| 39 | " | —CHPh$_2$ | —Cl | —I | 0.75 | An(7.5) | NaI(0.36) | rt | 2 | 0.82 | — |
| 40 | —CH$_2$OPh | " | —I | —OH | 0.82 | DMSO(7.5)H$_2$O(1.9) | Cu$_2$O(0.62) | 40 | 3 | 0.22 | 30 |

TABLE III (Part 3)

$$\text{(Ia)} \quad \underset{COOR^2}{\overset{R^1}{\underset{N}{\bigcirc}}}\text{NCHCCH}_2Y \longrightarrow \underset{COOR^2}{\overset{R^1}{\underset{N}{\bigcirc}}}\text{NCHCCH}_2X \quad \text{(I)}$$

| No. | R¹ | R² | Y | X | Ia (g) | Solvent (ml) | Reagent (g) | Temp (°C.) | Time (hr) | Yield (g) | (%) |
|---|---|---|---|---|---|---|---|---|---|---|---|
| 41 | —Ph | —CHPh₂ | —I | —ONO₂ | 0.72 | DMSO(7.2) | NaNO₃(2.1)CH₃O₃SC₆H₄CH₃-p | 55 | 0.5 | 0.56 | 88 |
| 42 | " | " | " | " | 0.10 | DMSO(1) | NaNO₃(0.3)(CH₃)₂SO₄(0.2) | 55 | 2 | — | 78 |
| 43 | " | " | " | " | 0.10 | DMSO(1) | NaNO₃(0.15)CH₃O₃SCH₃(0.073) | 55 | 1.5 | — | 81 |
| 44 | " | " | " | " | 0.10 | DMSO(1) | NaNO₃(0.15)C₂H₅O Ts(0.15) | 55 | 1.5 | — | 72 |
| 45 | " | " | " | " | 0.10 | DMSO(1) | NaNO₃(0.3)(CH₂Cl)₂(0.4) | 55 | 30 | — | 75 |
| 46 | —CH₂Ph | —C₄H₉-t | " | " | 3.49 | An(70) | NaNO₃(0.3)i-C₅H₁₁ONO₂ | 55 | 2 | 3.10 | — |
| 47 | —Ph | —CHPh₂ | —I | —OH | 0.10 | An:H₂O(2:1) (7) | AgNO₃(1.29) | rt | 1 | OH=1 ONO₂=3 | ratio |
| 48 | " | " | " | —ONO₂ | | | AgNO₃(0.06)CaCO₃(0.035) | rt | 0.5 | 0.09 | 50 |
| 49 | —CH₂Ph | " | " | —ONO₂ | 0.22 | An(2.2) | AgNO₃(0.067) | rt | 1 | 0.05 | — |
| 50 | —Ph | " | —Br | —OCHO | 0.053 | CH₂Cl₂(3) | HCOOH(0.039)[(CH₃)₂N]₂CNH (0.115) | rt | 1.5 | | |
| 51 | " | " | —I | —OCOCF₃ | 0.5 | HCON(CH₃)₂(8) | AgOCOCF₃(0.21) | rt | 1 | 0.45 | 92 |
| 52 | " | " | —Cl | —SC₆H₅ | 2.03 | An(12)CH₃OH(4) | PhSNa(0.8)PhSH(0.8) | 5 | 3 | 1.50 | 64 |
| 53 | " | " | —Br | " | 0.44 | An(7.5)CH₃OH(2.5) | PhSNa(0.25)PhSH(0.25) | rt | 1 | 0.40 | 80 |
| 54 | " | " | " | CH₃—N⎯⎯N ‖ ‖ —S⎯⎯N | 0.40 | CH₃OH(8) | CH₃—N⎯⎯N ‖ ‖ NaS⎯⎯N | 35 | 3.5 | 0.28 | 59 |

TABLE III (Part 4)

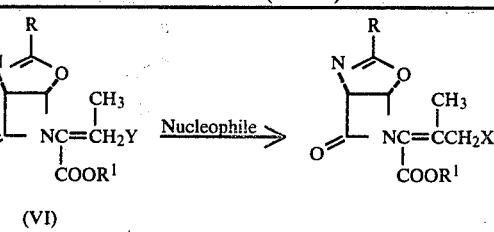

| No. | R | R[1] | Y | X | Start Mat (g) | Solvent (ml) | Reagent (g) | Temp. (°C.) | Time (hr) | Crop; (g) | Yield (%) |
|---|---|---|---|---|---|---|---|---|---|---|---|
| 1 | Ph— | —CH$_2$Ph | —Cl | —OAc | 0.060 | DMF(2) | CH$_3$COONa(0.023) CH$_3$COOK(0.035) | rt | 21 | 0.036 | 57 |
| 2 | " | " | " | " | 0.062 | CH$_3$CN(4) | Dibenzo-18-crown-6 (0.007) HCOONa(0.031) | " | 7 | 0.045 | 69 |
| 3 | " | " | " | —OCHO | 0.062 | CH$_3$CN(4) | Dibenzo-18-crown-6 (0.007) HCOOK(0.40) | 50 | 19 | 0.029 | 46 |
| 4 | " | " | " | " | 0.329 | CH$_3$CN(20) | Dibenzo-18-crown-6 (0.04) | refl | 35 (min.) | 0.215 | 64 |
| 5 | " | " | " | —I | 0.689 | CH$_3$COCH$_3$(10) | NaI(0.58) | rt | 20 (min.) | 0.840 | — |
| 6 | " | " | —I | —OCHO | 0.840 | DMF(7) | HCCONa(0.23) | " | 3 | 0.623 | 88 |

DMF = N,N-dimethylformamido

Table IV (Part 1)

Physical Constants of

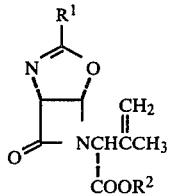

| No. | R[1] | R[2] | mp. (°C.) | IR: $\nu_{max}^{CHCl_3}$ cm$^{-1}$ | NMR: $\delta^{CDCl_3}$ (Hz value = coupling constant) |
|---|---|---|---|---|---|
| 1 | —Ph | —H | 161-163 | — | 1.93d(1Hz)3H, 4.86s1H, 5.23brs2H, 5.36d(3Hz)1H, 6.2d (3Hz)1H, 7.3-8.2m5H. |
| 2 | " | —CH$_3$ | — | 1785,1753, 1634. | 1.88d(1Hz)3H, 3.62s3H, 4.86s1H, 5.17m1H, 5.27m1H, 5.40d (3.5Hz)1H, 6.07d(3.5Hz)1H, 7.4–7.7m;7.9–8.2m)5H. |
| 3 | " | —CH$_2$Ph | 67-68 | 1785,1750, 1660, 1640. | 1.83brs3H, H, 4.85s1H, 5.10m3H, 5.20m1H, 5.33d(3Hz)1H, 6.00d(3Hz)1H, 7.2-8.0m10H. |
| 4 | " | —CH$_2$C$_6$H$_4$NO$_2$-p | 86.5-88 | 1790,1760, 1639,1510, 1340. | 1.90d(1Hz)3H, 4.92s1H, 5.13d(1Hz)1H, 5.28d(1Hz)1H, 5.17s2H, 5.28d(3Hz)1H, 6.03d(3Hz)1H. |
| 5 | " | —CHPh$_2$ | 117-118 | 1773,1735, 1628. (in Nujol) | 1.79d(1.5Hz)3H, 4.92s1H, 5.07brs1H, 5.17d(1.5Hz)1H, 5.32d(3Hz)1H, 5.93d(3Hz)1H, 6.88s1H, 7.2-8.0m15H. |
| 6 | —CH$_2$Ph | —C,H$_9$-t | 63-65 | 2960,1771, 1735,1640. | 1.46s9H, 1.78s3H, 3.71s2H, 4.56s1H, 4.96-5.23m3H 5.83d(4Hz)1H, 7.30s5H. |
| 7 | " | —CH$_2$Ph | — | 1788,1748, 1647,1172. | 1.73brs3H, 3.60s2H, 4.73s1H, 4.98brs1H, 5.10brs1H, 5.12s2H, 5.09d(3.8Hz)1H, 5.73d(3.8Hz)1H, 7.27-7.33m10H. |
| 8 | " | —CHPh$_2$ | 99.5-100 | 1784,1752, 1647,1171. | 1.70brs3H, 3.52s2H, 4.82s1H, 4.96s1H, 5.08d(3.8Hz)1H, 5.10brs1H, 5.73d(3.8Hz)1H, 6.92s1H, 7.25s5H, 7.32s10H. |
| 9 | —CH$_2$OPh | " | — | 1788,1749, 1658,1601, 1173. | 1.78brs3H, 4.67s1H, 4.80s1H, 5.05brs1H, 5.18s2H, 5.13-5.23m2H, 5.88d1H, 6.83-7.44m10H. |
| 10 | —C$_6$H$_4$—CH$_3$-p | " | 138-139 | 1780,1750, 1630. | 1.77d(0.5Hz)3H, 2.38s3H, 4.92s1H, 5.07m1H, 5.18m1H, 5.32 d(3Hz)1H, 6.00d(3Hz)1H, 6.92s1H. |
| 11 | —C$_6$H$_4$OCH$_3$-p | " | 107-108 | 2840,1780, 1750,1630, 1610. | 1.80d(0.5Hz)3H, 3.83s3H, 4.92s1H, 5.07m1H, 5.18m1H, 5.32d(3Hz)1H, 5.98d(3Hz)1H, 6.90s1H. |
| 12 | —C$_6$H$_4$NO$_2$-p | " | 133-135 | 1785,1750, 1640,1600, 1530,1350. | 1.83d(0.5Hz)3H, 4.97s1H, 5.10m1H, 5.25m1H, 5.40d(3Hz)1H, 6.04d(3Hz)1H, 6.88s1H, 8.10A$_2$B$_2$4H. |
| 13 | —C$_6$H$_4$Cl-p | " | 130-131 | 1780,1750, 1630,1600. | 1.80d(0.5Hz)3H, 4.92s1H, 5.05brs1H, 5.18m1H, 5.32d(3Hz) 1H, 5.98d(3Hz)1H, 6.87s1H. |
| 14 | —C$_6$H$_4$CN-p | " | 148°-149° | 2240,1780, 1750,1630, | 1.83brs3H, 4.97s1H, 5.08brs1H, 5.23m1H, 5.40d(3Hz)1H, 6.07d(3Hz)1H, 6.88s1H, 7.80A$_2$B$_2$4H. |

Table IV (Part 1)-continued

Physical Constants of (structure with $R^1$, oxazoline ring, COOR$^2$, NCHCCH$_3$ group)

| No. | $R^1$ | $R^2$ | mp. (°C.) | IR: $\nu_{max}^{CHCl_3}$ cm$^{-1}$ | NMR: $\delta^{CDCl_3}$ (Hz value = coupling constant) |
|-----|-------|-------|-----------|-----------------------------------|-------------------------------------------------------|
|     |       |       |           | 1610.                             |                                                       |

Table IV (Part 2)

Physical constants of (structure with $R^1$, oxazoline ring, COOR$^2$, NCHCCH$_2$X group)

| No. | $R^1$ | $R^2$ | X | mp. (°C.) | IR: $\nu_{max}^{CHCl_3}$ cm$^{-1}$ | NMR: $\delta^{CDCl_3}$ (Hz value = coupling constant) |
|-----|-------|-------|---|-----------|-----------------------------------|-------------------------------------------------------|
| 1 | —Ph | —CH$_3$ | —Br | glass | 1788,1753,1640. | 3.55s3H, 3.98s2H, 4.97s1H, 5.28d(3Hz)1H, 5.32s1H, 5.55s1H, 5.90d(3Hz)1H, (7.1–7.4+7.7–7.9)m5H. |
| 2 | " | —CH$_2$CCl$_3$ | " | — | — | 4.12s2H, 5.20s1H, (4.58d+4.92d)ABq(12Hz)1H, 5.40d(4Hz)1H, 5.58s1H, 5.78s1H, 6.06d(4Hz)1H, 7.1–8.1m5H. |
| 3 | " | —CH$_2$Ph | —Cl | — | 1780,1747,1630. | 4.17s2H, (4.98d+5.23d)ABq(10Hz)2H, 5.10s1H, 5.27–5.43m2H, 5.62s1H, 6.03d(4Hz)1H, 7.05–8.09m10H. |
| 4 | " | " | —Br | — | — | TLC: Rf=0.18 (C$_6$H$_6$/CH$_3$COOC$_2$H$_5$(4:1)/SiO$_2$ plate) |
| 5 | " | " | —I | — | 1785,1752,1735. | 4.00s2H, (5.00d+5.23d)ABq(12Hz), 5.10s1H, 5.33+5.67)s1H, 5.37d(3Hz)1H, 6.02d(3Hz)1H, 7.2–8.1m10H. |
| 6 | " | " | —OH | — | — | 3.05brs1H, 4.15s2H, 4.97s1H, (4.97d+5.25d)ABq(12Hz)1H, (5.23+5.43)s1H, 5.27d(3Hz)1H, 6.02d(3Hz)1H, 7.2–8.0m10H. |
| 7 | " | —CHPh$_2$ | —Cl | 105–106 | 1784,1751,1633. | 4.13s2H, 5.17s1H, 5.35s1H, 5.62s1H, 5.38d(3Hz)1H, 6.03d(3Hz)1H, 6.93s1H, 7.2–8.1m15H. |
| 8 | " | " | —Br | foam | 1788,1757,1636. | 4.03s2H, 5.15s1H, 5.27s1H, 5.58s1H, 5.33d(3Hz)1H, 6.00d(3Hz)1H, 6.90s1H, (7.1–7.3m+7.8–8.0m)15H. |
| 9 | " | " | —I | — | 1783,1752,1632, 1602,1173. | 3.92s2H, 5.15s1H, 5.12s+5.53s1H, 5.27d(4Hz)1H, 5.90d(4Hz)1H, 6.85s1H, 7.2–7.4m, 7.8–8.0m. |
| 10 | " | " | —OH | — | 3370,1782,1755, 1635. | 2.50–3.35brs1H, 4.18s2H, 5.08s1H, 5.22s1H, 5.28d(3Hz)1H, 5.50s1H, 6.08d(3Hz)1H, 6.93s1H, 7.2–8.0m15H. |
| 11 | " | " | —OCOCF$_3$ | — | 1785,1747,1634, 1604,1173. | 4.72s2H, 5.03s1H, 5.33s+5.53brs1H, 5.35m1H, 6.02d(3Hz)1H, 6.90s1H, 7.2–7.5m, 7.7–8.0m. |
| 12 | " | " | —ONO$_2$ | — | — | 4.95s2H, 5.03s1H, 5.32d(3.5Hz)1H, (5.43brs+5.58brs)1H, 6.00d(3.5Hz)1H, 6.90s1H, 7.2–7.5m, 7.0–8.0m. |
| 13 | " | " | —SPh | — | 1787,1755,1636. | 3.55s2H, 5.00s1H, 5.13d(3Hz)1H, 5.17s1H, 5.30s1H, 5.63d(3Hz)1H, 6.80s1H, 6.95–8.0m20H. |
| 14* | " | " | —S(O)Ph | — | 1786,1752,1634. | 3.25s2H, 5.00s1H, 5.12–5.42m3H, (5.92d+6.02)(3Hz)1H, 6.80s1H, 6.95–8.0m20H. |
| 15 | " | " | (tetrazole-S- with N-CH$_3$) | — | 1788,1758,1637. | 3.65s3H, 3.97s2H, 5.03s1H, 5.13s1H, 5.50s1H, 5.23d(3Hz)1H, 5.93d(3Hz)1H, 6.75s1H, (7.1–7.14m+7.6–7.8m)15H. |

*Prepared from Compound No. 13 by oxidation with m-chloroperbenzoic acid.

Table IV (Part 3)

Physical constants of

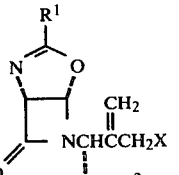

| No. | R¹ | R² | X | mp. (°C.) | IR: $\nu_{max}^{CHCl_3}$ cm$^{-1}$ | NMR: $\delta^{CDCl_3}$ (Hz value = coupling constant) |
|---|---|---|---|---|---|---|
| 1 | —Ph | —CH₂—C₆H₄—NO₂ | —Cl | — | 1788,1756,1678, 1633,1610,1580. | 4.12s2H, 5.02s1H, 5.27d(3Hz)1H, 5.48d(12Hz)1H, 5.90d(3Hz)1H, 7.10–8.03m9H, 5.05s2H. |
| 2 | —Ph | —CH₂—C₆H₄—NO₂ | —Br | — | — | TLC: Rf = 0.35 (C₆H₆/CH₃COOC₂H₅(2:1)/ SiO₂ plate) |
| 3 | —CH₂Ph | —C₄H₉-t | —Cl | 63–66 | 2975,1792,1742, 1650. | 1.45s9H, 3.73s2H, 4.06s2H, 4.76s1H, 5.11d(4Hz)1H, 5.41d(10Hz)2H, 7.31s5H. |
| 4 | " | " | —I | 55–56 | 2970,1785,1742 1649. | 1.48s9H, 3.76s2H, 3.95s2H, 4.81s1H, 5.16d(4Hz)1H, 5.45d(18Hz)2H, 5.83d(4Hz)1H, 7.33s5H. |
| 5 | " | " | —ONO₂ | — | — | 1.45s9H, 3.73s2H, 4.61s2H, 5.16d(4Hz)1H, 5.50d(6Hz)2H, 5.85d(4Hz)1H, 7.30s5H, 4.91s2H. |
| 6 | " | " | —OH | 86–89 | 2940,1780,1742, 1650. | 1.45s9H, 3.71s2H, 4.10s2H, 4.63s1H, 5.03–5.20m2H, 5.36s1H, 5.86d(4Hz)1H, 7.31s5H. |
| 7 | " | —CH₂Ph | —Cl | 87–88 | 1787,1751,1648 1607. | 3.62s2H, 4.03s2H, 4.93s1H, 5.15m3H, 5.25s1H, 5.50s1H, 5.90d(3Hz)1H, 7.08–7.45m10H. |
| 8 | " | " | —I | 92–99 | 1785,1749,1644 | 3.63s2H, 3.87s2H, 4.93s1H, 5.13s2H, 5.33d(24H)2H, 5.10d(4Hz)1H, 5.75d(4Hz)1H. |
| 9 | " | " | —OH | 69–70.5 | 3608,1780,1750, 1647,1604. | 2.13brs1H, 3.63s2H, 4.10s2H, 4.82s1H, 5.10–5.17m4H, 5.35s1H, 5.83d(3.5Hz)1H, 7.20–7.50m10H. |
| 10 | " | —CHPh₂ | —Cl | 82–83 | 1740,1751,1645, 1602. | 3.55s2H, 4.02s2H, 5.03s1H, 5.12d(3Hz)1H, 5.18s1H, 5.50s1H, 5.72d(3Hz)1H, 6.92s1H, 7.15–7.45m15H. |
| 11 | " | " | —I | glass | 1784,1749,- 1643, 1603. | 3.55s2H, 3.87s2H, 5.03–5.08m3H, 5.48s1H, 6.90s1H, 7,03–7.53m15H. |
| 12 | " | " | —OH | 40–55 | 3608,3430br,1780, 1749,1645,1602. | 2.67brs1H, 3.56s2H, 4.07brs2H, 4.90s1H, 5.05brs2H, 5.35s1H, 5.75d(3Hz)1H, 6.90s1H, 7.08–7.48m15H. |
| 13 | " | " | —ONO₂ | glass | 1785,1747,1642, 1602,1278. | 3.55s2H, 4.85ABq3H, 5.12d(4Hz)1H, 5.33s1H, 5.52s1H, 5.75d(4Hz), 6.93s1H, 7.07–7.57m15H. |
| 14 | —CH₂OPh | —CH₂—C₆H₄—NO₂ | —OCOCH₃ | — | 1790,1750 | 2.07s3H, 4.67s2H, 4.77s2H, 5.02s1H, 5.23–5.37m3H, 5.30s2H, 5.57brs1H, 6.00d(3Hz)1H, 6.85–7.33m5H, 7.53–8.27q(8Hz)4H. |
| 15 | " | —CHPh₂ | " | — | 3005,1785,1745, 1605,1595,1495. | 1.98s3H, 4.60s2H, 4.66s2H, 5.03s1H, 5.22d(2.4Hz)1H, 5.28brs1H, 5.52brs1H, 5.93d(2.4Hz)1H, 6.97s1H, 6.8–7.7m15H. |

Table IV (Part 4)

Physical constants of

| No. | R¹ | R² | X | mp. (°C.) | IR: $\nu_{max}^{CHCl_3}$ cm$^{-1}$ |
|---|---|---|---|---|---|
| 1 | —CH₂OPh | —CHPh₂ | —Cl | — | 3010,1790,1750, 1605,1590,1495. |
| 2 | " | " | —OCHO | — | 1790,1750,1730. |
| 3 | " | " | —OH | — | 3600–3200,1785, 1745. |
| 4 | —C₆H₄NO₂-p | " | —Cl | 163–165 | 1790,1748,1640. |
| 5 | " | " | —I | 161–162 | 1788,1750,1631. |
| 6 | " | " | —OH | — | 1785,1745,1635. |

Table IV (Part 4)-continued

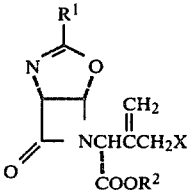

Physical constants of

| No. | R¹ | | X | mp.(°C.) | IR: $\nu_{max}^{CHCl_3}$ cm$^{-1}$ |
|---|---|---|---|---|---|
| 7 | —C$_6$H$_4$CH$_3$-p | " | —Cl | 132–133 | 1790,1752,1632. |
| 8 | " | " | —I | 135–136 | 1775,1743,1668. |
| 9 | " | " | —·OH | 127–128.5 | 1780,1750,1630. |
| 10 | —C$_6$H$_4$CN-p | " | —Cl | 145–147 | 2230,1788,1751, 1635,1612. |
| 11 | " | " | —I | 148–150 | 2228,1785,1752, 1635,1611. |
| 12 | " | " | —OH | 135–136 | 3450,2230,1785, 1750,1635,1610. |
| 13 | —C$_6$H$_4$Cl-p | " | —Cl | 134–135 | 1785,1752,1633, 1600. |
| 14 | " | " | —I | 137–139 | 1785,1752,1635, 1600. |
| 15 | " | " | —OH | — | — |

| No. | NMR: $\delta^{CDCl_3}$ (Hz value = coupling constant) |
|---|---|
| 1 | 4.11s2H, 4.60s2H, 5.09s1H, 5.21d(3Hz)1H, 5.24s1H, 5.58 brs1H, 5.87d(3Hz)1H, 6.93s1H, 6.7–7.7m15H. |
| 2 | 4.63s2H, 4.74s2H, 5.03s1H, 5.26d(3Hz)1H, 5.33brs1H, 5.57s1H, 5.95d(3Hz)1H, 6.99s1H, 6.8–7.6m15H, 7.84s1H. |
| 3 | 4.18s2H, 4.63s2H, 5.03s1H, 5.19s1H, 5,29d(3Hz)1H, 5.48s1H, 5.98d(3Hz)1H, 6.98s1H, 6.8–7.7m15H. |
| 4 | 4.15s2H, 5.30s1H, 5.40d(3Hz)1H, 5.40d(26Hz)2H, 6.03d(3Hz) 1H, 6.83s1H, 7.13–8.50m14H. |
| 5 | 4.00s2H, 5.18s1H, 5.40d(3Hz)1H, 5.43d(28Hz)2H, 6.01sd(3Hz) 1H, 6.85s1H, 7.10–8.40m14H. |
| 6 | ----------TLC: Rf 0.2 (C$_6$H$_6$:CH$_3$COOC$_2$H$_5$(1:1)) |
| 7 | 2.40s3H, 4.11s2H, 5.28s1H, 5.31d(3Hz)1H, 5.35d(26Hz)2H, 5.96d(3Hz)1H, 6.88s1H, 7.06–7.96m14H. |
| 8 | 2.40s3H, 3.96s2H, 5.15s1H, 5.31d(3Hz)1H, 5.38d(26Hz)2H, 5.95d(3Hz)1H, 6.88s1H, 7.06–7.95m14H. |
| 9 | 2.40s3H, 4.16d(4Hz)2H, 5.21s1H, 5.25d(24Hz)2H, 5.30d (3Hz)1H, 6.03d(3Hz)1H, 6.90s1H, 7.08–8.36m14H. |
| 10 | 4.12s2H, 5.15s1H, 5.28s1H, 5.37d(3Hz)1H, 5.58s1H, 6.02d (3Hz)2H, 6.83s1H, 7.1–7.4m10H, (7.63d + 7.95d)ABq(8Hz)4H. |
| 11 | 3.97s2H, 5.15s2H, 5.35d(3Hz)1H, 5.63s1H, 5.93d(3Hz)1H, 6.82s1H, 7.2–7.4m10H, (7.63d + 7.93d)ABq(8Hz)4H. |
| 12 | 4.22d(5Hz)2H, 5.12s1H, 5.23s1H, 5.37d(3Hz)1H, 5.48s1H, 6.12d(3Hz)1H, 6.90s1H, 7.2–7.5m10H, (7.67d + 7.97d) ABg(8Hz)4. |
| 13 | 4.12s2H, 5.13s1H, 5.28s1H, 5.31d1H, 5.57s1H, 5.93d (3Hz)1H, 6.87s1H, 7.2–7.5m12H, 4.67d(9Hz)2H. |
| 14 | 3.98s2H, 5.17s2H, 5.32d(3Hz)1H, 5.62s1H, 5.98d(3Hz)1H, 6.87s1H, 7.1–7.5m12H, 7.80d(7Hz)2H. |
| 15 | 3.2br1H, 4.17brs2H, 5–5.4m3H, 5.41–5.47m1H, 6.00d(3Hz) 1H, 6.83s1H, 7–7.3m12H, 7.77d(8Hz)2H. |

Table IV (Part 5)

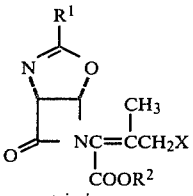

Physical constants of

Following pairs are the geometric isomers:
Nos. 1 and 2; 3 and 4; 5 and 6; 8 and 9;
(11 and 12; and 13 and 14.)

| No. | R¹ | R² | X | mp.(°C.) | IR: $\nu_{max}^{CHCl_3}$ cm$^{-1}$ |
|---|---|---|---|---|---|
| 1. | —Ph | —CH$_3$ | —Br | — | 1790,1733,1636. |
| 2. | " | " | " | — | 1790,1733,1636. |
| 3. | " | —CH$_2$CCl$_3$ | —Br | — | — |
| 4. | " | " | " | — | — |
| 5. | " | —CH$_2$Ph | —Cl | foam | 1786,1726,1632. |
| 6. | " | " | " | " | 1786,1726,1632. |
| 7. | " | " | —I | — | — |
| 8. | " | " | —OCHO | — | 1780,1725,1630. |
| 9. | " | " | " | — | — |
| 10. | " | " | —OCOCH$_3$ | — | 1780,1740,1630. |

Table IV (Part 5)-continued

Physical constants of 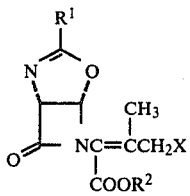

Following pairs are the geometric isomers:
Nos. 1 and 2; 3 and 4; 5 and 6; 8 and 9;
(11 and 12; and 13 and 14.)

| No. | | | | | |
|---|---|---|---|---|---|
| 11. | " | —CHPh$_2$ | —Cl | foam | 1780,1728,1665. |
| 12. | " | " | " | " | 1780,1728,1665. |
| 13. | " | " | —Br | " | 1789,1730,1633. |
| 14. | " | " | " | " | 1789,1730,1633. |
| 15. | " | " | —OCHO | — | 1788,1730,1633, 1603,1580. |
| 16. | —CH$_2$Ph | —CH$_2$Ph | —Cl | — | 1781,1741,1644, 1602. |

| No. | NMR: $\delta^{CDCl_3}$ (Hz value = coupling constant) |
|---|---|
| 1. | 1.93s3H, 3.78s3H, (4.37d + 4.68d)ABq(10Hz)2H, 5.48d(3Hz)1H 5.51d(3Hz)1H. |
| 2. | 2.35s3H, 3.70s3H, (3.95d + 4.08d)ABq(10Hz)2H, 6.25d(3Hz) 1H, 6.29d(3Hz)1H. |
| 3. | 2.02s3H, (4.35d + 4.76d)ABq(10Hz)2H, (4.70d + 5.06d)ABq(13 Hz)2H, 5.52d(4Hz)1H, 6.36d(4Hz)1H, 7.05-8.15msH. |
| 4. | 2.45s3H, (3.80d + 4.10d)ABq(10Hz)2H, (4.67d + 5.03d)Abq(13 Hz)2H, 5.52d(4Hz)1H, 6.35d(4Hz)1H, 7.05-8.15m5H. |
| 5. | 1.93s3H, (4.43d + 4.77d)ABq(12Hz)2H, 4.9-5.4ABq2H, 5.38d (3Hz)1H, 6.15d(3Hz)1H, 7.2-8.1m10H. |
| 6. | 2.30s3H, (3.92 + 4.15d)ABq(12Hz)2H, 4.9-5.4ABq2H, 5.38d (3Hz)1H, 6.15d(3Hz)1H, 7.2- 8.1m10H. |
| 7. | 2.37s3H, (3.87d + 4.07d)ABq(9Hz)2H, (5.07d + 5.27d)ABq(13 Hz)2H, 5.42d(4Hz)1H, 6.23d(4Hz)1H, 7.9-8.2m10H. |
| 8. | (1.82s + 2.20s)3H, 4.65s3H/2, 4.9-5.4m5H/2, 5.30d(4Hz)1H. 6.07d(4Hz)1H, 7.2-8.0m11H. |
| 9. | 2.20s3H, 4.73s2H, (5.10d + 5.33d)ABq(12Hz)2H, 5.40d(4Hz) 1H, 6.17d(4Hz)1H, 7.27-8.07m11H. |
| 10. | (1.83s + 1.95s)3H, (2.07s + 2.20s)3H, 4.67s1H, 5.0 − 5.5m3H, 5.43d(4Hz)1H, 6.20d(4Hz)1H, 7.3-8.1m10H. |
| 11. | 2.27s3H, (3.86d + 4.12d)ABq(11Hz)2H, 5.33d(3Hz)1H, 6.00d (3Hz)1H, 6.87s1H, 7.12-7.97m15H. |
| 12. | 1.92s3H, (4.28d + 4.70d)ABq(11Hz)2H, 5.33d(3Hz)1H, 6.00d (3Hz)1H, 6.90s1H, 7.12-7.97m15H. |
| 13. | 1.95s3H, (4.18d + 4.63d)ABq(10Hz)2H, 5.37d(3Hz)1H, 6.08d (3Hz)1H, 6.98s1H, 7.1-8.0m15H. |
| 14. | 2.31s3H, (3.77d + 4.07d)ABq(10Hz)1H, 5.37d(3Hz)1H, 6.08d (3Hz)1H, 6.92s1H, 7.1-8.0m15H. |
| 15. | (1.83s + 2.16s)3H, (4.7s + 5.23s)2H, (5.35d + 5.40d)(3Hz)1H, 6.80d(3Hz)1H, (6.93s + 6.95s)1H, 7.1-7.6m13H, 7.7-8.1m3H. |
| 16. | (1.68s + 2.25s)3H, (3.63s + 3.55s)2H, (3.80s + 4.77s)2H, 5.10-5.20m4H, (5.93d + 6.12d)dd(3Hz)1H, 7.15-7.53m10H. |

What we claim is:

1. A process for the preparation of a compound of the formula:

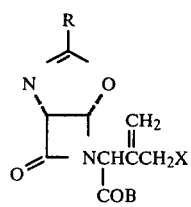

which comprises heating a penicillin 1-oxide of the following formula:

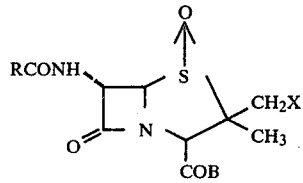

wherein
R represents (a) 1-6 C alkyl, (b) 7-15 C aralkyl, (c) 7-15 C heterocyclicalkyl, (d) 7-9 C aryloxyalkyl, (e) 7-9 C heterocyclicoxyalkyl, (f) 6-10 C aryl, (g) 6-10 C heterocyclic, (h) 1-6 C alkoxy, (i) 7-15 C aralkoxy, (j) 7-15 C heterocyclicalkoxy, (k) 6-10 C aryloxy, (l) 6-10 C heterocyclicoxy, (m) carbamoyl, or (n) 2-7 C carbalkoxy, each of said groups being unsubstituted or substituted by hydroxy, 1-6 C alkanoyloxy, 1-3 C alkoxy, 7-9 C aralkoxy, 6-8 C aryloxy, oxo, amino, 1-3 C alkylamino, 1-5 C alkanoylamino, nitro, 1–3 C alkyl, 6–10 C aryl, carboxy, protected carboxy, cyano or halo, X represents (a) halo, (b) hydroxy, (c) up to 5 C acyloxy selected from the group of nitrooxy, sulfurous acyloxy, formyloxy, acetoxy, propionyloxy, trifluoroacetoxy, β-hydroxypropionyloxy, α-haloacetyloxy, benzyloxy, nicotinoyloxy, carbamoyloxy, methoxycarbonylox, aminopropionyloxy, sulfenyloxy and sulfinyloxy, (d) 1–6 C alkoxy, (e) thiocarbamoylthio, (f) 1–5 C alkylthio, (g) 6–9 C arylthio, (h) 6–9 C heterocyclicthio, or (i) 1–6 C sulfinyl, the aryl portion of the groups R and X and the substituents thereof being selected from the group of phenyl and naphthyl and the heterocyclic portion of the groups R and X being selected from the group consisting of furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyrozinyl, as-triazinyl, quinolyl, isoquinolinyl, and 2-benzothiazolyl.

COB is carboxy or protected carboxy, and wherein the S→O and C—CH$_3$ bonds are in the cis positions with respect to each other.

2. A process according to claim 1, wherein the reaction is carried out in the presence of a desulfurizing reagent.

3. A process according to claim 1, wherein the reaction is carried out in the presence of a dehydrating reagent.

4. A process according to claim 1, wherein R is phenyl, COB is carboxy and X is hydrogen.

* * * * *